US011633425B2

(12) United States Patent
Cohen et al.

(10) Patent No.: US 11,633,425 B2
(45) Date of Patent: Apr. 25, 2023

(54) ANTI-GLYCATION COMPOSITIONS

(71) Applicant: AHAVA—DEAD SEA LABORATORIES LTD., Lod (IL)

(72) Inventors: Dror Cohen, Kibbutz Ein Gedi (IL); Meital Portugal Cohen, Jerusalem (IL); Alexandra Blinderman, Kibutz Almog (IL); David Barak, Modi'in (IL); Ma'or Ze'Evi, Kibbutz Kalia (IL)

(73) Assignee: AHAVA—DEAD SEA LABORATORIES LTD., Lod (IL)

( * ) Notice: Subject to any disclaimer, the term of this patent is extended or adjusted under 35 U.S.C. 154(b) by 0 days.

(21) Appl. No.: 17/319,446

(22) Filed: May 13, 2021

(65) Prior Publication Data

US 2022/0362289 A1 Nov. 17, 2022

(51) Int. Cl.
| | |
|---|---|
| A61K 36/00 | (2006.01) |
| A61K 35/08 | (2015.01) |
| A61K 8/9789 | (2017.01) |
| A61K 8/96 | (2006.01) |
| A61K 36/28 | (2006.01) |
| A61K 36/328 | (2006.01) |
| A61K 36/725 | (2006.01) |
| A61Q 19/08 | (2006.01) |

(52) U.S. Cl.
CPC .............. *A61K 35/08* (2013.01); *A61K 8/965* (2013.01); *A61K 8/9789* (2017.08); *A61K 36/28* (2013.01); *A61K 36/328* (2013.01); *A61K 36/725* (2013.01); *A61Q 19/08* (2013.01)

(58) Field of Classification Search
CPC .................................................... A61Q 19/08
See application file for complete search history.

(56) References Cited

U.S. PATENT DOCUMENTS

| | | | |
|---|---|---|---|
| 6,800,292 B1 | 10/2004 | Murad | |
| 6,871,805 B2 * | 3/2005 | Samelson | A61K 33/00 241/23 |
| 7,435,432 B2 | 10/2008 | Olson | |
| 7,666,442 B2 | 2/2010 | Morariu | |
| 8,591,874 B2 | 11/2013 | Oblong et al. | |
| 8,846,019 B2 | 9/2014 | Lintner et al. | |
| 8,877,259 B2 | 11/2014 | Florence et al. | |
| 9,511,034 B1 | 12/2016 | Garrett | |
| 10,064,813 B2 | 9/2018 | Florence et al. | |
| 10,512,603 B2 | 12/2019 | Alminana Domenech et al. | |
| 10,722,461 B2 | 7/2020 | Burnam | |
| 10,806,707 B2 | 10/2020 | Finley et al. | |
| 10,813,910 B2 | 10/2020 | Parachur et al. | |
| 10,842,733 B2 | 11/2020 | Florence et al. | |
| 2003/0007939 A1 | 1/2003 | Murad | |
| 2003/0049255 A1 | 3/2003 | Sims et al. | |
| 2006/0002929 A1 | 1/2006 | Khare et al. | |
| 2007/0203240 A1 | 8/2007 | Oblong et al. | |
| 2008/0044373 A1 | 2/2008 | Ilekti et al. | |
| 2009/0093440 A1 | 4/2009 | Murad | |
| 2011/0044920 A1 | 2/2011 | Hines et al. | |
| 2013/0078202 A1 | 3/2013 | Abdul-Malak et al. | |
| 2013/0323228 A1 | 12/2013 | Norman | |
| 2016/0346191 A1 | 12/2016 | Petkoska et al. | |
| 2020/0214955 A1 | 7/2020 | Varotto | |

FOREIGN PATENT DOCUMENTS

| | | | |
|---|---|---|---|
| BR | 201005274 A2 * | 4/2013 | |
| CN | 102671118 A | 9/2012 | |
| CN | 104352870 A | 2/2015 | |
| CN | 104383417 A | 3/2015 | |
| CN | 104800772 A | 7/2015 | |
| CN | 107252471 A | 10/2017 | |
| CN | 104706553 B * | 6/2018 | |
| CN | 104673486 B * | 7/2018 | ........... A61K 36/185 |
| CN | 109364220 A | 2/2019 | |
| CN | 110720473 A | 1/2020 | |
| EA | 033620 B1 | 11/2019 | |
| EP | 1 074 245 A2 | 2/2001 | |
| EP | 2 174 648 A1 | 4/2010 | |
| EP | 3 398 585 B1 | 2/2020 | |
| IL | 232044 B | 8/2020 | |
| JP | 2002205913 A | 7/2002 | |
| JP | 2002212046 A | 7/2002 | |
| JP | 2002370963 A | 12/2002 | |
| JP | 2003026581 A | 1/2003 | |
| RU | 2228771 C1 | 5/2004 | |
| RU | 2253433 C2 | 6/2005 | |
| TW | I469778 B | 1/2015 | |
| WO | 2002/069963 A2 | 9/2002 | |

(Continued)

OTHER PUBLICATIONS

Myrrh-Wikipedia, accessed on Aug. 3, 2022, pp. 1-6 (Year: 2022).*
Ghimire et al, Jujube (*Ziziphus jujuba* Mill.) fruit feeding extends lifespan and increases tolerance to environmental stresses by regulating aging-associated gene expression in *Drosophila*. Biogerontology, (20170400) vol. 18, No. 2, pp. 263-273 (Year: 2017).*
Narda et al., "Novel Facial Cream Containing Carnosine Inhibits Formation of Advanced Glycation End-Products in Human Skin", Skin Pharmacology and Physiology, 2018, 31 (6), 324-331.
Shin et al., "Anti-glycation activities of phenolic constituents from *Silybum marianum* (Milk Thistle) flower in vitro and on human explants", Molecules, 2015, 20 (3), 3549-3564.
Chandler et al., "Effects of plant-derived polyphenols on TNF-alpha and nitric oxide production induced by advanced glycation end products" Mol. Nutr. Food Res., 2010, 54, S141-S150.
Wu et al., "Silymarin: a novel antioxidant with antiglycation and anti-inflammatory properties in vitro and in vivo", Antioxid. Redox. Signal., 2011, 14, 353-366.

(Continued)

*Primary Examiner* — Qiuwen Mi

(74) *Attorney, Agent, or Firm* — Vorys, Sater, Seymour and Pease LLP; Anthony P. Venturino; Maryellen Feehery Hank

(57) ABSTRACT

This present invention discloses compositions comprising Dead Sea extract in combination with one or more plant extracts, uses thereof and methods of preventing and/or reducing and/or inhibiting the glycation of one or more biomolecules and/or preventing and/or reducing and/or inhibiting the formation of Advanced Glycation End Products.

32 Claims, 8 Drawing Sheets

(56) References Cited

FOREIGN PATENT DOCUMENTS

WO    2015/030702 A2    3/2015
WO    2016/123475 A1    8/2016

OTHER PUBLICATIONS

Alhusban et al., "Silymarin Ameliorates Diabetes-Induced Proangiogenic Response in Brain Endothelial Cells through a GSK-3β Inhibition-Induced Reduction of VEGF Release", J. Diabetes Res., 2017, :2537216. doi: 0.1155/2017/2537216. Epub Oct. 25, 2017.

Awasthia et al., "Silybin, a flavonolignan from milk thistle seeds, restrains the early and advanced glycation end product modification of albumin", RSC Adv., 2015, 5, 87660-87666.

Portugal-Cohen et al., "Dead Sea minerals: New findings on skin and the biology beyond". Experimental Dermatology, 2019, 28 (5), 585-592.

Lipotec, retrieved online at: https://na.lipotec.com [accessed online Oct. 6, 2021], 3 pages.

Glycerolate of Myrrh, retrieved online at: www.knowde.com/stores/solabia-group/products/glycerolat-of-myrrh, activeorganics.com, 2021, 2 pages.

Maruzen Pharmaceuticals Co., Ltd., Jujube, retrieved online at: www.maruzenpcy.co.jp/english/jiten/sholjujube.html, 2021, 2 pages.

Valencia et al., "Advanced glycation end product ligands for the receptor for advanced glycation end products: biochemical characterization and formation kinetics", Analytical Biochemistry, 2004, 324, 68-78.

Sajithlal et al., "Advanced glycation end products induce crosslinking of collagen in vitro", Biochimica et Biophysica Acta, 1998, 1407, 215-224.

Huang et al., "High-Throughput Assay of Oxygen Radical Absorbance Capacity (ORAC) Using a Multichannel Liquid Handling System Coupled with a Microplate Fluorescence Reader in 96-Well Format", J. Agric. Food Chem., 2002, 50 (16), 4437-4444.

Ott et al., "Role of advanced glycation end products in cellular signaling", Redox Biology, 2014, 2, 411-429.

Perrone et al., "Advanced Glycation End Products (AGEs): Biochemistry, Signaling, Analytical Methods, and Epigenetic Effects", Oxidative Medicine and Cellular Longevity, 2020, vol. 2020, Article ID: 3818196, 18 pages.

Jeanmaire et al., "Glycation during human dermal intrinsic and actinic ageing: an in vivo and in vitro model study", British Journal of Dermatology 2001, 145 (1), 10-18.

Sotoudeh et al., "The anti-diabetic and antioxidant effects of a combination of Commiphora mukul, Commiphora myrrha and Terminalia chebula in diabetic rats", Avicenna Journal of Phytomedicine, 2019, 9 (5), 454-464.

Huseini et al.,"The Efficacy of *Silybum marianum* (L.) Gaertn. (silymarin) in the Treatment of Type II Diabetes: A Randomized, Double-blind, Placebo-controlled, Clinical Trial", Phytotherapy Research: An International Journal Devoted to Pharmacological and Toxicological Evaluation of Natural Product Derivatives, 2006, 20 (12), 1036-1039.

\* cited by examiner

ANTI-GLYCATION COMPOSITIONS

FIELD OF THE INVENTION

This invention relates to compositions comprising Dead Sea extract in combination with one or more plant extracts and their uses.

BACKGROUND OF THE INVENTION

Advanced Glycation End Products (AGEs) are modified biomolecules such as proteins, lipids and nucleic acids that had passed a non-enzymatic oxidizing glycation process, activated by reducing sugars. AGEs accumulate in normal cells during aging and may be increased due to pathologies such as diabetics, obesity and renal failure.

In recent years, a greater understanding of how AGEs affect the structure and functionality of the skin has brought into prominence the potential of anti-AGE strategies for the development of anti-aging cosmeceutical compounds [1].

Constituents from *Silybum marianum* (Milk Thistle) flower, Silymarin and the flavonolignan Silybin were shown to have anti-glycation activity [2]-[8].

REFERENCES

[1] Narda, M.; Peno-Mazzarino, L.; Krutmann, J.; Trullas, C.; Granger, C., Novel Facial Cream Containing Carnosine Inhibits Formation of Advanced Glycation End-Products in Human Skin. *Skin Pharmacology and Physiology* 2018, 31 (6), 324-331.

[2] Shin, S.; Lee, J.-A.; Kim, M.; Kum, H.; Jung, E.; Park, D., Anti-glycation activities of phenolic constituents from *Silybum marianum* (Milk Thistle) flower in vitro and on human explants. *Molecules* 2015, 20 (3), 3549-3564.

[3] Dave Chandler et. al., Effects of plant-derived polyphenols on TNF-alpha and nitric oxide production induced by advanced glycation end products. Mol. Nutr. Food Res. 2010, 54, S141-S150.

[4] Chi-Hao Wu et. al., Silymarin: a novel antioxidant with antiglycation and anti-inflammatory properties in vitro and in vivo. Antioxid. Redox. Signal. 2011, 14, 353-366.

[5] Ahmed Alhusban et. al., Silymarin Ameliorates Diabetes-Induced Proangiogenic Response in Brain Endothelial Cells through a GSK-3β Inhibition-Induced Reduction of VEGF Release. J. Diabetes Res. 2017, :2537216. doi: 10.1155/2017/2537216. Epub 2017 Oct. 25.

[6] Saurabh Awasthia and N. T. Saraswathi., Silybin, a flavonolignan from milk thistle seeds, restrains the early and advanced glycation end product modification of albumin. RSC Adv. 2015, 5, 87660-87666.

[7] TWI 469778.

[8] US 2013/0078202.

[9] U.S. Pat. No. 6,871,805.

[10] Portugal-Cohen, M.; Cohen, D.; Ish-Shalom, E.; Laor-Costa, Y.; Ma'or, Z. e., Dead Sea minerals: New findings on skin and the biology beyond. *Experimental dermatology* 2019, 28 (5), 585-592.

[11] na.lipotec.com

[12] activeorganics.com/

[13] www.knowde.com/stores/solabia-group/products/glycerolat-of-myrrh

[14] www.maruzenpcy.co.jp/english/jiten/sho/jujube.html

[15] U.S. Pat. No. 10,722,461.

[16] US 2007/0203240.

[17] U.S. Pat. No. 10,512,603.

[18] RU 2253433 C2.

[19] EP 1 074 245.

[20] US 2006/0002929.

[21] US 2003/0049255.

[22] EA 033620.

[23] US 2003/007939.

[24] U.S. Pat. No. 6,800,292.

[25] US 2009/093440.

[26] WO 2002/069963.

[27] US 2008/0044373.

[28] US 2020/0214955

[29] U.S. Pat. No. 10,842,733.

[30] JP 2002370963.

[31] JP 2002212046.

[32] WO 2015/030702.

[33] U.S. Pat. No. 9,511,034.

[34] U.S. Pat. No. 8,846,019.

[35] EP 3,398,585.

[36] U.S. Pat. No. 7,435,432.

[37] U.S. Pat. No. 7,666,442.

[38] US 2011/0044920.

[39] Jessica V. Valencia et. al.; Advanced glycation end product ligands for the receptor for advanced glycation end products: biochemical characterization and formation kinetics. *Analytical Biochemistry* 2004, 324, 68-78.

[40] G. B. Sajithlal et. al.; Advanced glycation end products induce crosslinking of collagen in vitro. *Biochimica et Biophysica Acta* 1998, 1407, 215-224.

[41] Huang, D.; Ou, B.; Hampsch-Woodill, M.; Flanagan, J. A.; Prior, R. L., High-throughput assay of oxygen radical absorbance capacity (ORAC) using a multichannel liquid handling system coupled with a microplate fluorescence reader in 96-well format. *Journal of agricultural and food chemistry* 2002, 50 (16), 443-4444.

Acknowledgement of the above references herein is not to be inferred as meaning that these are in any way relevant to the patentability of the presently disclosed subject matter.

SUMMARY OF THE INVENTION

The inventors of the present disclosure have developed active combinations of Dead Sea extract and natural plants extracts.

As the present application will further disclose, the combinations comprise a natural salt-concentrated extract from the Dead Sea and at least one extract from the Myrrh tree. The inventors have surprisingly found that each of the Dead Sea extract and the Myrrh tree extract is beneficially capable of inhibiting the formation of AGEs. The effect was illustrated both with the protein Bovine Serum Albumin (BSA) and with the skin protein collagen.

The combinations of the present disclosure may further comprise at least one *Silybum* extract or at least one Jujube extract.

The inventors have surprisingly found that a combination of the three extracts (at times referred to herein also as "triplex" or "triplex combination") selected from at least one Dead Sea extract, at least one Myrrh tree extract and at least one *Silybum* extract, significantly inhibited the formation of AGEs. The inventors illustrated the significant contribution of the Dead Sea extract to this inhibition effect. In addition, the triplex combination exhibited beneficial anti-oxidation properties which are beneficial both to the skin (e.g., assisting in reducing oxidative stress) and to the stability of the compositions while being exposed to air e.g., upon use and during storage. The inventors have surprisingly found that while the Dead Sea extract alone exhibited an insignificant anti-oxidation capability, the presence thereof in the aforementioned triplex improved the anti-oxidation effect illustrated with a combination of only the bi-component Myrrh tree extract and *Silybum* extract.

The inventors have also surprisingly found that while *Silybum* extract was expected to illustrate an inhibition effect on AGEs formation in a skin related model utilizing the skin protein collagen, no such effect was observed for this individual extract. Surprisingly, the AGEs formation inhibition effect of the aforementioned triplex combination was not attenuated by the *Silybum* extract as the triplex combination with the at least one Dead Sea extract, at least one Myrrh tree extract and at least one *Silybum* extract illustrated a significant and efficient inhibition effect of AGEs formation.

Furthermore, the inventors have surprisingly found that combinations in which in addition to the at least one Dead Sea extract, at least one Myrrh tree extract and at least one *Silybum* extract, a further extract being at least one Jujube extract was present, either lost their AGEs formation inhibition ability or illustrated a less significant effect. Similarly, the inventors have surprisingly found that combinations in which in addition to the at least one Dead Sea extract, at least one Myrrh tree extract and at least one Jujube extract, a further extract being at least one *Silybum* extract was present, either lost their AGEs formation inhibition ability or illustrated a less significant effect.

The AGEs formation inhibition effect illustrated by the combinations of the present disclosure provides it with beneficial attributes to the skin inter-alia counteracting the damage from the natural aging process and from the assault of daily environmental aggressors that may result for example from skin exposure to external oxidative stress, originated for example from UV radiation, cigarettes smoke and urban pollution, as well as by intrinsic stressors such ad tense or junk food.

Similarly, AGE-modified collagen and elastin are known as having modified biomechanical properties leading to loss of elasticity and increased stiffening, changes that promote the appearance of wrinkles. Glycation is also known as modifying the interaction of collagen with cells affecting their functions such as migration, differentiation and proliferation. It is known that glycated elastin is present in photo-aged skin suggesting ultraviolet irradiation stimulates glycation of elastin. Additionally, glycated extracellular matrix proteins seem to be more resistant to degradation by matrix metalloproteinases, thus slowing down its removal and replacement by newly synthesized and functional protein. The AGEs formation inhibition effect illustrated by the combinations of the present disclosure provides them with the beneficial ability to prevent and/or inhibit one or more of the above unfavorable phenomena associated with AGEs. Non-limiting examples of skin conditions that my be improved by topical application of the compositions of the present disclosure are one or more of skin wrinkles, skin fine-lines, skin elasticity, skin sagging, skin firmness, skin plumping, skin smoothness, skin roughness, skin pigmentation, un-even skin tone, skin photo-aging, skin appearance, skin detoxification or any combination thereof.

Accordingly, the compositions of the present disclosure may be beneficially used for treating or preventing one or more skin condition/s and/or disorder/s and/or diseases associated with biomolecules glycation and AGEs formation.

Thus, in one of its aspects, the present invention provides a composition comprising (i.e., as an active combination) at least one Dead Sea extract and at least one Myrrh tree extract.

In another one of its aspects the present invention provides a composition comprising, as an active ingredient, at least one Dead Sea extract and at least one Myrrh tree extract.

In a further one of its aspects the present invention provides a composition comprising, (e.g., as active ingredient/s), at least one Dead Sea extract and at least one Myrrh tree extract, wherein the composition may further comprise at least one *Silybum* extract and/or at least one Jujube extract.

In yet a further one of its aspects the present invention provides a composition comprising, (e.g., as active ingredient/s), at least one Dead Sea extract and at least one Myrrh tree extract, wherein the composition may further comprise at least one *Silybum* extract or at least one Jujube extract.

Yet, in a further one of its aspects the present invention provides a composition comprising, (e.g., as active ingredient/s), at least one Dead Sea extract and at least one Myrrh tree extract, wherein the composition may further comprise at least one *Silybum* extract and at least one Jujube extract, wherein the at least one *Silybum* extract and the at least one Jujube extract are present in said compositions at concentrations that are beneficial to the anti-glycation performance of the composition (e.g., preventing and/or reducing and/or inhibiting the glycation of one or more biomolecules, and/or preventing and/or reducing and/or inhibiting the formation of AGEs).

In another one of its aspects the present invention provides a composition comprising, (e.g., as active ingredient/s), at least one Dead Sea extract and at least one Myrrh tree extract, wherein said composition further comprises at least one *Silybum* extract.

In a further one of its aspects the present invention provides a composition comprising, (e.g., as active ingredient/s), at least one Dead Sea extract and at least one Myrrh tree extract, wherein said composition further comprises and at least one *Silybum* extract, wherein said composition is substantially free of Jujube extract.

In yet a further one of its aspects the present invention provides a composition comprising, (e.g., as active ingredient/s), at least one Dead Sea extract and at least one Myrrh tree extract, wherein said composition further comprises at least one *Silybum* extract and wherein said composition is free of Jujube extract.

Yet, in a further one of its aspects the present invention provides a composition comprising, (e.g., as active ingredient/s), at least one Dead Sea extract and at least one Myrrh tree extract, wherein said composition further comprises at least one Jujube extract.

In a further one of its aspects the present invention provides a composition comprising, (e.g., as active ingredient/s), at least one Dead Sea extract and at least one Myrrh tree extract, wherein said composition further comprises at least one Jujube extract and wherein said composition is substantially free of *Silybum* extract.

In a further one of its aspects the present invention provides a composition comprising, (e.g., as active ingredient/s), at least one Dead Sea extract and at least one Myrrh tree extract, wherein said composition further comprises at least one Jujube extract and wherein said composition is free of *Silybum* extract.

In another one of its aspects the present invention provides an anti-glycation composition comprising as an active combination at least one Dead Sea extract and at least one Myrrh tree extract.

In a further one of its aspects the present invention provides an anti-glycation composition comprising as an active combination at least one Dead Sea extract, at least one Myrrh tree extract, wherein said composition further comprises at least one *Silybum* extract and/or at least one Jujube extract.

In yet a further one of its aspects the present invention provides an anti-glycation composition comprising as an active combination at least one Dead Sea extract, at least one Myrrh tree extract, wherein said composition further comprises at least one *Silybum* extract or at least one Jujube extract.

Yet, in a further one of its aspects the present invention provides an anti-glycation composition comprising as an active combination at least one Dead Sea extract, at least one Myrrh tree extract, at least one *Silybum* extract and at least one Jujube extract, wherein the at least one *Silybum* extract and the at least one Jujube extract are present in said compositions at concentrations that are beneficial to the anti-glycation performance of the composition.

In another one of its aspects the present invention provides an anti-glycation composition comprising as an active combination at least one Dead Sea extract, at least one Myrrh tree extract and at least one *Silybum* extract.

In a further one of its aspects the present invention provides an anti-glycation composition comprising as an active combination at least one Dead Sea extract, at least one Myrrh tree extract and at least one *Silybum* extract, wherein said combination is substantially free Jujube extract.

In yet a further one of its aspects the present invention provides an anti-glycation composition comprising as an active combination at least one Dead Sea extract, at least one Myrrh tree extract and at least one *Silybum* extract, wherein said combination is free of Jujube extract.

Yet, in a further one of its aspects the present invention provides an anti-glycation composition comprising as an active combination at least one Dead Sea extract, at least one Myrrh tree extract and at least one Jujube extract.

In a further one of its aspects the present invention provides an anti-glycation composition comprising as an active combination at least one Dead Sea extract, at least one Myrrh tree extract and at least one Jujube extract, wherein said combination is substantially free of *Silybum* extract.

In a further one of its aspects the present invention provides an anti-glycation composition comprising as an active combination at least one Dead Sea extract, at least one Myrrh tree extract and at least one Jujube extract, wherein said combination is free of *Silybum* extract.

In another one of its aspects the present invention provides a composition/combination according to the invention for preventing and/or reducing and/or inhibiting the glycation of one or more biomolecules.

In another one of its aspects the present invention provides a composition/combination according to the invention for use in preventing and/or reducing and/or inhibiting the glycation of one or more biomolecules.

In another one of its aspects the present invention provides a composition/combination according to the invention for use in a method of preventing and/or reducing and/or inhibiting the glycation of one or more biomolecules, the method comprises administrating (e.g., topical application) said compositions/combinations to a subject in need thereof.

In a further one of its aspects the present invention provides a composition/combination according to the invention for preventing and/or reducing and/or inhibiting the formation of AGEs.

In a further one of its aspects the present invention provides a composition/combination according to the invention for use in preventing and/or reducing and/or inhibiting the formation of AGEs.

In a further one of its aspects the present invention provides a composition/combination according to the invention for use in a method of preventing and/or reducing and/or inhibiting the formation of AGEs, the method comprises administrating (e.g., topical application) said composition/combination to a subject in need thereof.

In another one of its aspects the present invention provides a composition/combination according to the invention for preventing and/or reducing and/or inhibiting the glycation of one or more biomolecules, and for preventing and/or reducing and/or inhibiting the formation of AGEs.

In another one of its aspects the present invention provides a composition/combination according to the invention for use in preventing and/or reducing and/or inhibiting the glycation of one or more biomolecules and preventing and/or reducing and/or inhibiting the formation of AGEs.

In another one of its aspects the present invention provides a composition/combination according to the invention for use in a method of preventing and/or reducing and/or inhibiting the glycation of one or more biomolecules and preventing and/or reducing and/or inhibiting the formation of AGEs, the method comprises administrating (e.g., topical application) said composition/combination to a subject in need thereof.

Yet, in a further one of its aspects the present invention provides a method of (substantially) preventing and/or (significantly) reducing and/or (significantly) inhibiting the glycation of one or more biomolecules, the method comprising topical application of a composition/combination according to the invention onto at least a region of the skin of a subject in need thereof.

In another one of its aspects the present invention provides a method of preventing and/or reducing and/or inhibiting the formation of AGEs, the method comprising topical application of a composition/combination according to the invention onto at least a region of the skin of a subject in need thereof.

In another one of its aspects the present invention provides a method of preventing and/or reducing and/or inhibiting the glycation of one or more biomolecules and for preventing and/or reducing and/or inhibiting the formation of AGEs, the method comprising topical application of a composition/combination according to the invention onto at least a region of the skin of a subject in need thereof.

Yet, in a further one of its aspects the present invention provides a method of increasing the effectiveness of a composition comprising at least one *Silybum* extract which is capable of preventing and/or reducing and/or inhibiting the formation of AGEs in the skin of a subject (e.g., a human subject), the method comprising including in the composition at least one Dead Sea extract and at least one Myrrh extract.

In a further one of its aspects the present invention provides a method of increasing the effectiveness of a composition comprising at least one Myrrh extract which is capable of preventing and/or reducing and/or inhibiting the formation of AGEs in the skin of a subject (e.g., a human subject), the method comprising including in the composition at least one Dead Sea extract and optionally at least one *Silybum* extract.

In a further one of its aspects the present invention provides a method of increasing the effectiveness of a composition comprising at least one Myrrh extract and at least one *Silybum* extract, the composition is capable of preventing and/or reducing and/or inhibiting the formation of AGEs in the skin of a subject (e.g., a human subject), the method comprising including in the composition at least one Dead Sea extract.

In a further one of its aspects the present invention provides a use of the composition/combination according to the invention for the manufacture of a formulation for preventing and/or reducing and/or inhibiting the glycation of one or more biomolecules, and/or for preventing and/or reducing and/or inhibiting the formation of AGEs.

In a further one of its aspects the present invention provides a use of the composition/combination according to the invention for the manufacture of a formulation for preventing and/or reducing and/or inhibiting the glycation of one or more biomolecules.

In a further one of its aspects the present invention provides a use of the composition/combination according to the invention for the manufacture of a formulation for preventing and/or reducing and/or inhibiting the formation of AGEs.

In a further one of its aspects the present invention provides a use of the composition/combination according to the invention for preventing and/or reducing and/or inhibiting the glycation of one or more biomolecules and preventing and/or reducing and/or inhibiting the formation of AGEs.

In a further one of its aspects the present invention provides a use of the composition/combination according to the invention for preventing and/or reducing and/or inhibiting the glycation of one or more biomolecules.

In a further one of its aspects the present invention provides a use of the composition/combination according to the invention for preventing and/or reducing and/or inhibiting the formation of AGEs.

Yet, in a further one of its aspects the present invention provides a composition/combination according to the invention for preventing and/or treating at least one disease or disorder of the skin of a subject, said disease or disorder being associate with and/or being induced by glycation of one or more biomolecules and/or by formation of AGEs.

In a further one of its aspects the present invention provides a use of the composition/combination according to the invention for the manufacture of a formulation for preventing and/or treating at least one disease or disorder of the skin of a subject, said disease or disorder being associate with and/or being induced by glycation of one or more biomolecules and/or by formation of AGEs.

In a further one of its aspects the present invention provides a method for treating and/or preventing at least one disease or disorder of the skin of a subject, wherein the disease or disorder being associate with and/or being induced by glycation of one or more biomolecules and/or formation of AGEs, the method comprises topical application of the composition/combination (or any formulation thereof) according to the invention onto (at least a region of) the skin of the subject in need thereof.

In another one of its aspects the present invention provides a method for protecting and/or improving the state of (at least a region of) the skin of a subject, preventing and/or treating imperfections of (at least a region of) the skin of a subject in need thereof, the method comprises topical application of the composition/combination (or any formulation thereof) according to the invention onto (at least a region of) the skin of the subject in need thereof, wherein the protecting and/or improving the state of the skin of a subject, preventing and/or treating imperfections of the skin of a subject in need thereof being associated with the composition/combination capability of preventing and/or reducing and/or inhibiting the glycation of one or more biomolecules, and/or with the composition capability of preventing and/or reducing and/or inhibiting the formation of AGEs.

In a further one of its aspects the present invention provides a method of substantially preventing or delaying the onset of, or substantially preventing or retarding the progression of a condition which is associated with the formation of AGEs in a subject (e.g., a human) in need thereof, the method comprises administering (e.g., topically) to the subject a composition/combination (or any formulation thereof) according to the invention.

Yet, in another one of its aspects, the present invention provides a serum, a lotion, an ointment, a gel, a shampoo, a moisturizer, a sunscreen, a cream, a stick, a spray, an aerosol, foam, a paste, a mousse, a solid, semi-solid, or a liquid make-up, a foundation, or a make-up comprising the composition/combination according to the invention.

In yet another one of its aspects, the present invention provides a serum, a lotion, an ointment, a gel, a moisturizer, a sunscreen, a cream, a stick, a spray, an aerosol, foam, a paste, a mousse, a liquid make-up, a foundation, or a make-up comprising the composition/combination according to the invention.

In another one of its aspects, the present invention provides a use of the composition/combination according to the invention for the preparation of a composition/formulation, the composition/formulation being selected from a cosmetic, skin-care, dermatological or a pharmaceutical composition/formulation.

In another one of its aspects the present invention provides compositions/combinations/formulations, compositions/combinations/formulations for use and methods of using compositions/combinations/formulations as herein described and exemplified.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF THE INVENTION

Figure 1:
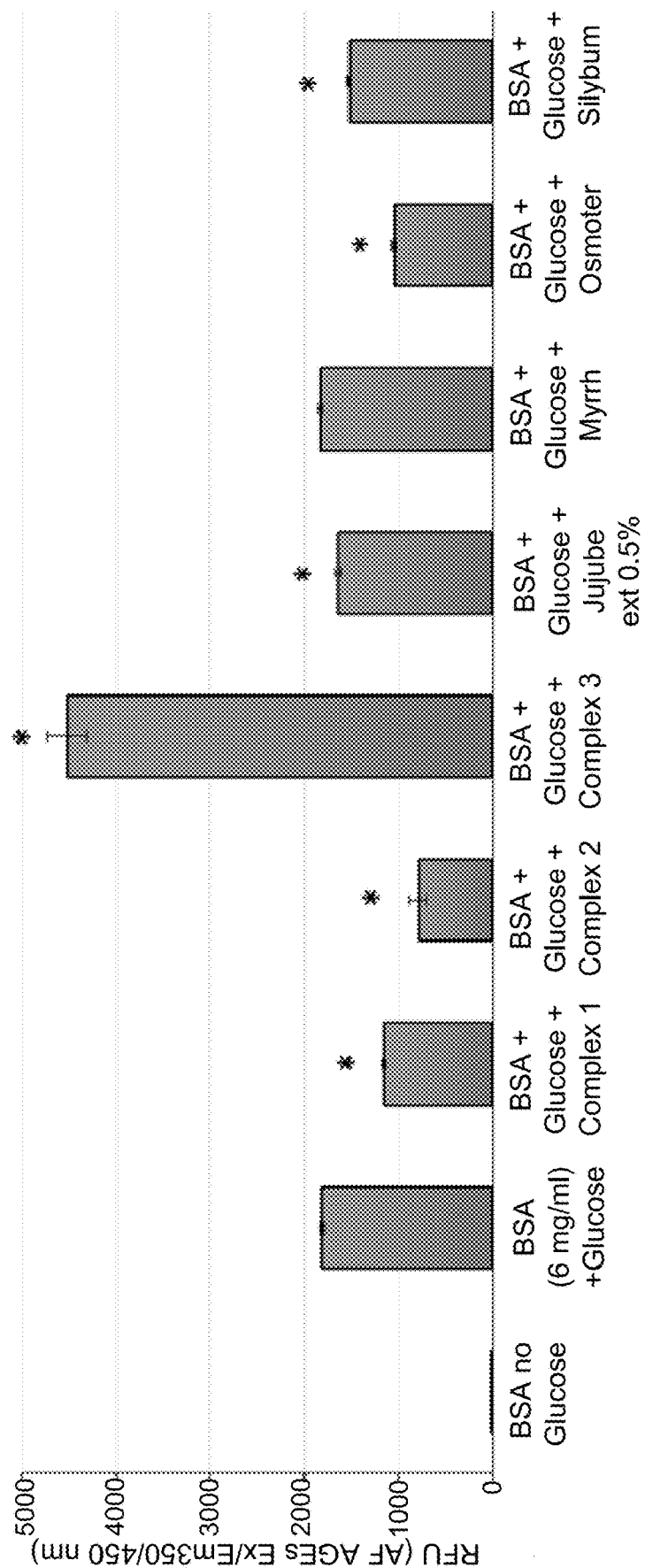
FIG. 1 illustrates auto-fluorescence results of AGEs generation utilizing a BSA assay as observed for various complexes, compositions, and extracts.

The present invention provides in one of its aspects a composition comprising as an active combination at least one Dead Sea extract and at least one Myrrh tree extract.

In some embodiments the composition may further comprise at least one *Silybum* extract and/or at least one Jujube extract.

As used herein the term "Dead Sea extract" refers to a mixture of natural materials obtained from the waters of the Dead Sea and/or the mud surrounding the Dead Sea and/or the soil bed of the Dead Sea.

In some embodiments the Dead Sea extract is a mixture of natural materials (e.g., salts, minerals) obtained from the waters of the Dead Sea.

In some embodiments the Dead Sea extract is Dead Sea water (herein abbreviated DSW) (or a concentrate thereof) or an aqueous solution having substantially the same salt and mineral content of the Dead Sea water (or a concentrate thereof).

In some embodiments, the Dead Sea extract is the Dead Sea water.

In some embodiments the "Dead Sea water" refers to the saline waters obtained from the Dead Sea (Israel or Jordan) region or an aqueous solution prepared by dissolving Dead Sea minerals and salts in an aqueous medium which simulate such natural solution, namely having substantially identical parameters characteristic of that measured for the natural DSW, said parameters being salts content/concentrations, minerals content/concentrations, cations and anions content/concentrations, ratio of divalent cations to monovalent cations, and optionally also one or more of TDS (Total Dissolved Salt, w/v), soluble natural substances, and other parameters known to define or characterize natural DSW.

In some embodiments, the Dead Sea extract is the Dead Sea water which may be obtained directly from the Dead Sea filtered water substantially having the same salt content (a hypersaline concentration) as that of the unfiltered Dead Sea water, or Dead Sea water treated by any one or more of various other methods employed to e.g., remove organic matter and residual contaminants therefrom.

It is noted that in some embodiments the Dead Sea extract is not an ultra fine Dead Sea mineral/s and/or salt/s that were forced through a conical screen mill e.g., such as those disclosed in [9] U.S. Pat. No. 6,871,805, the content of which is incorporated herein by reference.

In some embodiments, the Dead Sea extract is an aqueous solution simulating the content of DSW i.e., having substantially identical content as that of DSW.

In some embodiments, the Dead Sea extract is an aqueous solution having substantially identical salts content, minerals content, salts concentration and mineral concentrations as that of DSW.

In some embodiments, the Dead Sea extract is an aqueous solution having substantially identical salts content, minerals content, salts concentration, minerals concentrations, concentration of a particular cation or anion, ratio of divalent cations to monovalent cations, TDS, soluble natural substances and other parameters known to define or characterize natural DSW.

In some embodiments, the Dead Sea extract is an aqueous solution simulating the salt content (a hypersaline concentration) of DSW i.e., having salt content substantially identical to that of DSW.

In some embodiments, the Dead Sea extract is an aqueous solution simulating the mineral content of DSW i.e., having mineral content substantially identical to that of DSW.

In some embodiments, the Dead Sea extract is an aqueous solution simulating the salt content (a hypersaline concentration) and the mineral content of DSW i.e., having salt content substantially identical to that of DSW, mineral content substantially identical to that of DSW and ratio of divalent cations to monovalent cations substantially identical to that of DSW.

In some embodiments, the Dead Sea water having:
1. a specific density of 1.25-1.35 g/ml,
2. pH=4.6-5.6 (at 25° C.), and/or
3. less than 100 cfu/g of non-pathogenic microbes.

The Dead Sea water having the above physical characteristics is a concentrated extract of Dead Sea water comprising (among other metal salt ions) $Ca^{+2}$, $Mg^{+2}$, $Na^+$ and $K^+$ and high concentrations of anions such as $Cl^-$ and $Br^-$.

In some embodiments, the DSW is a clear colorless viscous liquid (at 25° C.).

In some embodiments, the concentrations of these ions are, as assessed by a water analysis carried out by the Geological Survey of Israel:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 1800-3200 mg/L
Potassium ($K^+$): 2,500 mg/L, and
Bromide ($Br^-$): 10,000-12,000 mg/L.
Other minerals may also exist in the waters.
In some embodiments, the Dead Sea Water comprises:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 2400-3200 mg/L
Potassium ($K^+$): 2,500 mg/L, and
Bromide ($Br^-$): 10,000-12,000 mg/L.
Other minerals may also exist in the waters.
In some embodiments, the Dead Sea Water comprises:
Calcium ($Ca^{+2}$): 5,000-10,000 mg/L
Chloride ($Cl^-$): 315,000-360,000 mg/L
Magnesium ($Mg+^2$): 100,000-150,000 mg/L
Sodium ($Na^+$): 1800-2200 mg/L
Potassium ($K^+$): 1,000-2,000 mg/L, and
Bromide ($Br^-$): 5,000-10,000 mg/L.
Other minerals may also exist in the waters.
In some further embodiments, the Dead Sea Water comprises:
Calcium ($Ca^{+2}$) 34,000-40,000 mg/L
Chloride ($Cl^-$) 320,000-370,000 mg/ L
Magnesium ($Mg^{+2}$) 90,000-95,000 mg/L
Potassium ($K^+$) 1,300-2,200 mg/L
Sodium ($Na^+$) 1,500-2,800 mg/L
Bromide ($Br^-$) 11,000-15,000 mg/L.
Other minerals may also exist in the waters.
In some embodiments, the Dead Sea Water comprises:
Calcium ($Ca^{+2}$): 38,000 mg/L
Chloride ($Cl^-$): 345,000 mg/L
Magnesium ($Mg+^2$): 92,500 mg/L
Sodium ($Na^+$): 2000 mg/L Strontium ($Sr^{+2}$): 800 mg/L
Potassium ($K^+$): 1,400 mg/L, and
Bromide ($Br^-$): 11,500 mg/L.
Other minerals may also exist in the waters.

In some embodiments, the Dead Sea Water comprises:
Calcium ($Ca^{+2}$): 38,000 mg/L
Chloride ($Cl^-$): 345,000 mg/L
Magnesium ($Mg^{+2}$): 92,500 mg/L
Sodium ($Na^+$): 2000 mg/L
Strontium ($Sr^{+2}$): 800 mg/L
Potassium ($K^+$): 1,400 mg/L, and
Bromide ($Br^-$): 11,500 mg/L.
Other minerals may also exist in the waters.

In some embodiments, the DSW is natural DSW which has undergone pre-treatment i.e., having been concentrated by allowing water to evaporate, for example through solar evaporation, thereafter reconstituted to afford a solution.

In some embodiments the Dead Sea extract is Dead Sea Water preparation commercially available as "Maris Sal" or "Maris Aqua" or "Aqua, Maris Sal" (AHAVA, Israel) referred to herein below also as "Osmoter". The therapeutic uses thereof are known in the art e.g., See [10].

The Osmoter is a concentrated Dead Sea water that has a high concentration of salts e.g., magnesium, calcium, strontium, bromine, boron and lithium which are characteristic Dead Sea minerals. The Osmoter has high ratio of divalent cations, mainly magnesium and calcium vs. monovalent cations, mainly potassium and sodium.

In some embodiments the ratio between the magnesium and calcium divalent cations to the potassium and sodium monovalent cations in the Osmoter is [92,500 mg/l+38,000 mg/l]/[1400 mg/l+2000 mg/l]=130,500/3400=38.38.

In some embodiments, the Osmoter is the product: Geological Survey—Ministry of National Infrastructures, State of Israel, especially for AHAVA-Dead Sea Laboratories CAS #INCI Monograph ID:11089), also known as Dead Sea Works LTD.

In some embodiments, the Osmoter comprises the following ions: $Mg^{+2}$ (92,500 mg/L), $Ca^{+2}$ (38,000 mg/L), $K^+$(1,400 mg/L), $Na^+$(2,000 mg/L), $Sr^{+2}$ (800 mg/L), $Cl^-$ (345,000 mg/L) and $Br^-$(11,500 mg/L). Other minerals may also exist in the Osmoter.

In some embodiments, the Osmoter has the following composition:

| | Salt normality (N) | |
|---|---|---|
| Na | 0.118 | (2.720 g/l) |
| K | 0.054 | (2.100 g/l) |
| Ca | 0.873 | (35.000 g/l) |
| Mg | 3.815 | (92.700 g/l) |
| Ba | $6.6 \times 10^{-5}$ | (0.009 g/l) |
| Cd | $<1.8 \times 10^{-7}$ | ($<2 \times 10^{-5}$ g/l) |
| Co | $<3.4 \times 10^{-5}$ | (<0.002 g/l) |
| Cu | $<3.15 \times 10^{-5}$ | (<0.004 g/l) |
| Cr | $<3.85 \times 10^{-4}$ | (<0.02 g/l) |
| Fe | $<3.58 \times 10^{-5}$ | (<0.002 g/l) |
| Li | $5.76 \times 10^{-3}$ | (0.040 g/l) |
| Mn | $1.82 \times 10^{-4}$ | (0.010 g/l) |
| Mo | $<1.04 \times 10^{-6}$ | ($<10^{-4}$ g/l) |
| Ni | $<3.4 \times 10^{-5}$ | (<0.002 g/l) |
| Pb | $<9.6 \times 10^{-8}$ | ($<2 \times 10^{-5}$) |
| Rb | $3.5 \times 10^{-6}$ | ($<3 \times 10^{-4}$ g/l) |
| Sb | $<1.6 \times 10^{-7}$ | ($<2 \times 10^{-5}$ g/l) |
| Sr | $7.6 \times 10^{-3}$ | (0.670 g/l) |
| V | $<7.9 \times 10^{-5}$ | (<0.004 g/l) |
| Th | $<8.6 \times 10^{-8}$ | ($<2 \times 10^{-5}$ g/l) |
| U | $<8.4 \times 10^{-8}$ | ($<2 \times 10^{-5}$ g/l) |
| Zn | $<3.06 \times 10^{-5}$ | (<0.002 g/l) |
| Cl | 9.75 | (346 g/l) |
| Br | 0.175 | (14 g/l) |
| B | 0.011 | (0.120 g/l) |
| As | $2.7 \times 10^{-5}$ | (0.002 g/l) |
| I | $6.30 \times 10^{-7}$ | ($8 \times 10^{-5}$ g/l) |
| SiO2 | $<3.33 \times 10^{-4}$ | (<0.02 g/l) |
| SiO4 | $<2.2 \times 10^{-3}$ | (<0.2 g/l) |

In some embodiments the ratio between the magnesium and calcium divalent cations to the potassium and sodium monovalent cations in the Dead Sea extract e.g., Dead Sea water, is between about 20 to about 55. At time is it about 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 51.0, 52.0, 53.0, 54.0 and about 55.0. In some embodiments said ratio is about 23.7, at times about 25.9, at times about 27.0, at times about 29.5, at times about 38.1, at times about 38.4, at times about 40.0, at time about 44.0, even at times about 53.6. Any value which is between any one of the above values is within the scope of the present disclosure.

In some embodiments the Dead Sea extract is Dead Sea mud.

In some embodiments the Dead Sea extract is typically an active fraction having by itself at least one attribute which may be enhanced in a combination with one or more of the plants extracts disclosed herein e.g., Myrrh tree extract, *Silybum* extract and Jujube extract.

In some embodiments the concentration of the Dead Sea extract (e.g., Dead Sea water) in the composition (or formulation) of the invention is at least about 0.01% (w/w). At time is it about 0.01%, 0.02%, 0.03%, 0.04%, 0.05%, 0.06%, 0.07%. 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%. 0.28%, 0.29%, 0.30%, 0.31%, 0.32%, 0.33%, 0.34%, 0.35%, 0.36%, 0.37%. 0.38%, 0.39%, 0.40%, 0.41%, 0.42%, 0.43%, 0.44%, 0.45%, 0.46%, 0.47%. 0.48%, 0.49%, 0.50%, 0.51%, 0.52%, 0.53%, 0.54%, 0.55%, 0.56%, 0.57%. 0.58%, 0.59%, 0.60%, 0.61%, 0.62%, 0.63%, 0.64%, 0.65%, 0.66%, 0.67%. 0.68%, 0.69%, 0.70%, 0.71%, 0.72%, 0.73%, 0.74%, 0.75%, 0.76%, 0.77%, 0.78%, 0.79%, 0.80%, 0.81%, 0.82%, 0.83%, 0.84%, 0.85%, 0.86%, 0.87%. 0.88%, 0.89%, 0.90%, 0.91%, 0.92%, 0.93%, 0.94%, 0.95%, 0.96%, 0.97%. 0.98%, 0.99%, 1.00%, 1.10%, 1.10%, 1.11%, 1.12%, 1.13%, 1.14%, 1.15%, 1.16%, 1.17%. 1.18%, 1.19%, 1.20%, 1.21%, 1.22%, 1.23%, 1.24%, 1.25%, 1.26%, 1.27%. 1.28%, 1.29%, 1.30%, 1.31%, 1.32%, 1.33%, 1.34%, 1.35%, 1.36%, 1.37%. 1.38%, 1.39%, 1.40%, 1.41%, 1.42%, 1.43%, 1.44%, 1.45%, 1.46%, 1.47%. 1.48%, 1.49%, 1.50%, 1.51%, 1.52%, 1.53%, 1.54%, 1.55%, 1.56%, 1.57%. 1.58%, 1.59%, 1.60%, 1.61%, 1.62%, 1.63%, 1.64%, 1.65%, 1.66%, 1.67%. 1.68%, 1.69%, 1.70%, 1.71%, 1.72%, 1.73%, 1.74%, 1.75%, 1.76%, 1.77%. 1.78%, 1.79%, 1.80%, 1.81%, 1.82%, 1.83%, 1.84%, 1.85%, 1.86%, 1.87%. 1.88%, 1.89%, 1.90%, 1.91%, 1.92%, 1.93%, 1.94%, 1.95%, 1.96%, 1.97%. 1.98%, 1.99%, 2.00%, 2.10%, 2.11%, 2.12%, 2.13%, 2.14%, 2.15%, 2.16%, 2.17%. 2.18%, 2.19%, 2.20%, 2.21%, 2.22%, 2.23%, 2.24%, 2.25%, 2.26%, 2.27%. 2.28%, 2.29%, 2.30%, 2.31%, 2.32%, 2.33%, 2.34%, 2.35%, 2.36%, 2.37%. 2.38%, 2.39%, 2.40%, 2.41%, 2.42%, 2.43%, 2.44%, 2.45%, 2.46%, 2.47%. 2.48%, 2.49% and about 2.50% (w/w). Any value which is between any one of the above values is within the scope of the present disclosure.

In some embodiments the concentration of the Dead Sea extract (e.g., Dead Sea water) in the composition (or formulation) of the invention is at between about 0.01% to about 2.40% (w/w), at times between about 0.01% to about 2.00% (w/w), at times between about 0.01% to about 1.50% (w/w), at times between about 0.01% to about 1.00% (w/w), at times between about 0.05% to about 2.40% (w/w), at times between about 0.05% to about 2.00% (w/w), at times between about 0.05% to about 1.50% (w/w), at times between about 0.05% to about 1.00% (w/w), at times between about 0.20% to about 2.40% (w/w), at times between about 0.20% to about 2.00% (w/w), at times between about 0.20% to about 1.50% (w/w), at times between about 0.20% to about 1.00% (w/w), inclusive the end points values.

In some embodiments the concentration of the Dead Sea extract (e.g., Dead Sea water) in the composition (or formulation) of the invention is about 0.1% (w/w).

In some embodiments the concentration of the Dead Sea extract (e.g., Dead Sea water) in the composition (or formulation) of the invention is about 0.2% (w/w).

In some embodiments the concentration of the Dead Sea extract (e.g., Dead Sea water) in the composition (or formulation) of the invention is about 0.5% (w/w).

In some embodiments the concentration of the Dead Sea extract (e.g., Dead Sea water) in the composition (or formulation) of the invention is about 1.0% (w/w).

In some embodiments the concentration of the Dead Sea extract (e.g., Dead Sea water) in the composition (or formulation) of the invention is about 2.0% (w/w).

The term "plan extract" is used herein in its broadest definition. The term relates to a fraction obtained from one or more parts e.g., roots, leaves, stems, seeds, fruits, flowers, shoot and barks (peel) of a plant and/or one or more of sap, latex, and resin of a plant, e.g., Myrrh tree extract, *Silybum* extract and Jujube extract. The extract is typically an active fraction having by itself at least one attribute which may be enhanced in a combination according to the invention. The extracts from the Myrrh tree, *Silybum* and Jujube are extracts obtained according to known procedures or are commercially available extracts, as disclosed. The extracts may be a pure (neat) extracts or extracts formulated along with a predetermined amount of an additive such as a stabilizer, diluent, carrier, filler, antioxidant or any other inert additive.

The origin of the at least one plant extract employed in the composition/combinations/formulations of the present invention is as noted below. For purposes herein, the plants from which the extracts are obtained may be those native to the designated origin or otherwise grown outside of this origin region, naturally, e.g., due to natural invasion, or for commercial purposes, horticulture purposes or for any other reason.

The "*Silybum*", also referred to as "*Silybum* milk thistle" is a genus of two species of thistles in the daisy family. The plants are native to Southern Europe through Asia and are presently found throughout the world. The most widespread species is *Silybum marianum*. This plant is an annual or biennial plant of the family Asteraceae with other common names, including cardus marianus, milk thistle, blessed milkthistle, Marian thistle, Mary thistle, Saint Mary's thistle, Mediterranean milk thistle, variegated thistle and Scotch thistle. This fairly typical thistle has red to purple flowers and shiny pale green leaves with white veins.

The *Silybum* extract may be obtained commercially. One such commercially available extract is the ACTIPHYTE™ MILK THISTLE GL80NP (Product Number: 344000-188), Produced & Commercialized by LIPOTEC USA, INC (manufactured by cold process extraction method), See [11, 12], and was used in some of the examples provided herein. This extract mainly consists of silymarin but also contains fatty acids, including linoleic acid. The silymarin is a complex mixture of polyphenolic molecules, including seven flavonolignans (Silybin A, Silybin B, Isosilybin A, Isosilybin B, Silychristin, Isosilychristin, Silydianin) and one flavonoid (Taxifolin) (Sourced from World Heritage Encyclopedia™ licensed under CC BY-SA 3.0.). This extract is specifically a *Silybum marianum* seeds extract having the following physical and chemical properties:

Contains 64% Glycerin (Source, Plant; Origin, USA, CAS #56-81-5), 20% *Silybum marianum* Extract (Source, Plant; Origin, China; CAS #84604-20-6) and 16% water (Mineral water; Origin, USA, CAS #7732-18-5);

Physical state—liquid;
Form—liquid;
Color—colorless to light yellow;
pH: 4-6.5 (25° C.);
Boiling point—290° C.;
Flash point—198.9° C.;
Relative density—1.15-1.25 (25° C.); and
Soluble in water.

The *Silybum* extract may be obtained from one or more parts of the plant as noted above.

In some embodiments the *Silybum* extract is *Silybum marianum* Extract (Source, Plant; Origin, China; CAS #84604-20-6).

In some embodiments the *Silybum* extract is *Silybum marianum* extract.

In some embodiments the *Silybum* extract is *Silybum marianum* seeds extract.

In some embodiments the *Silybum* extract is an extract obtained from the *Silybum* seeds.

In some embodiments the *Silybum* extract is an aqueous extract.

In some embodiments the *Silybum* extract is a water-soluble extract.

In some embodiments the *Silybum* extract is not to be considered as an essential oil.

In some embodiments the *Silybum* extract is not to be considered as *Silybum* oil.

In some embodiments the *Silybum* extract is not an oil extract.

In some embodiments the *Silybum* extract extract is typically an active fraction having by itself at least one attribute which may be enhanced in a combination with the Dead Sea extract and/or with the Myrrh extract.

In some embodiments the concentration of the *Silybum* extract (e.g., *Silybum marianum* seeds extract) in the composition/combination (or formulation) of the invention is at least about 0.01% (w/w). At time is it about 0.01%, 0.02%, 0.03%, 0.04%, 0.05%, 0.06%, 0.07%. 0.08%, 0.09%, 0.10%, 0.11%, 0.12%, 0.13%, 0.14%, 0.15%, 0.16%, 0.17%. 0.18%, 0.19%, 0.20%, 0.21%, 0.22%, 0.23%, 0.24%, 0.25%, 0.26%, 0.27%. 0.28%, 0.29%, 0.30%, 0.31%, 0.32%, 0.33%, 0.34%, 0.35%, 0.36%, 0.37%. 0.38%, 0.39%, 0.40%, 0.41%, 0.42%, 0.43%, 0.44%, 0.45%, 0.46%, 0.47%. 0.48%, 0.49%, 0.50%, 0.51%, 0.52%, 0.53%, 0.54%, 0.55%, 0.56%, 0.57%. 0.58%, 0.59%, 0.60%, 0.61%, 0.62%, 0.63%, 0.64%, 0.65%, 0.66%, 0.67%. 0.68%, 0.69%, 0.70%, 0.71%, 0.72%, 0.73%, 0.74%, 0.75%, 0.76%, 0.77%. 0.78%, 0.79%, 0.80%, 0.81%, 0.82%, 0.83%, 0.84%, 0.85%, 0.86%, 0.87%. 0.88%, 0.89%, 0.90%, 0.91%, 0.92%, 0.93%, 0.94%, 0.95%, 0.96%, 0.97%. 0.98%, 0.99%, 1.00%, 1.10%, 1.10%, 1.11%, 1.12%, 1.13%, 1.14%, 1.15%, 1.16%, 1.17%. 1.18%, 1.19%, 1.20%, 1.21%, 1.22%, 1.23%, 1.24%, 1.25%, 1.26%, 1.27%. 1.28%, 1.29%, 1.30%, 1.31%, 1.32%, 1.33%, 1.34%, 1.35%, 1.36%, 1.37%. 1.38%, 1.39%, 1.40%, 1.41%, 1.42%, 1.43%, 1.44%, 1.45%, 1.46%, 1.47%. 1.48%, 1.49%, and 1.50% (w/w). Any value which is between any one of the above values is within the scope of the present disclosure.

In some embodiments the concentration of the *Silybum* extract (e.g., *Silybum marianum* seeds extract) in the composition/combination (or formulation) of the invention is at between about 0.01% to about 1.50% (w/w), at times between about 0.01% to about 1.00% (w/w), at times between about 0.01% to about 0.50% (w/w), at times between about 0.05% to about 1.50% (w/w), at times between about 0.05% to about 1.00% (w/w), at times between about 0.05% to about 0.50% (w/w), at times between about 0.20% to about 1.50% (w/w), at times between about 0.20% to about 1.00% (w/w), at times between about 0.20% to about 0.50% (w/w), at times between about 0.50% to about 1.50% (w/w), at times between about 0.50% to about 1.00% (w/w), inclusive the end points values.

In some embodiments the concentration of the *Silybum* extract (e.g., *Silybum marianum* seeds extract) in the composition (or formulation) of the invention is about 0.05% (w/w).

In some embodiments the concentration of the *Silybum* extract (e.g., *Silybum marianum* seeds extract) in the composition (or formulation) of the invention is about 0.10% (w/w).

In some embodiments the concentration of the *Silybum* extract (e.g., *Silybum marianum* seeds extract) in the composition (or formulation) of the invention is about 0.15% (w/w).

In some embodiments the concentration of the *Silybum* extract (e.g., *Silybum marianum* seeds extract) in the composition (or formulation) of the invention is about 0.20% (w/w).

In some embodiments the concentration of the *Silybum* extract (e.g., *Silybum marianum* seeds extract) in the composition (or formulation) of the invention is about 0.50% (w/w).

In some embodiments the concentration of the *Silybum* extract (e.g., *Silybum marianum* seeds extract) in the composition (or formulation) of the invention is about 1.00% (w/w).

In some embodiments the concentration of the *Silybum* extract (e.g., *Silybum marianum* seeds extract) in the composition (or formulation) of the invention is about 1.50% (w/w).

The "Myrrh tree" is a large shrub (or small tree) indigenous to Northeast Africa and collected in Southern Arabia and Iran. In some embodiments the "Myrrh tree" is *Commiphora Myrrha* tree in the Burseraceae family. The tree is used in the production of Myrrh, a resin made from dried tree sap. Myrrh mostly contains terepenic essence as germacrene and elements; gums such as arabinose, galactose and methylglucurunoid acid; polysaccharides and resins. Several studies found that Myrrh was able to reduce the proliferation or replication of human cancer cells and inhibit growth in eight different types of cancer cells (specifically gynecological, skin and breast cancers). Myrrh has the ability to increase the function of white blood cells, which is critical for wound healing. It can also be used for minor skin irritations or wounds, such as athlete's foot, ringworm, or minor cuts.

The Myrrh tree extract may be obtained commercially. One such commercially available extract is Glycerolat® of Myrrh, Produced & Commercialized by CEP-SOLABIA Group See [13]. This extract is specifically an aqueous extract obtained from the resin of Myrrh *Commiphora abyssinica*, the extract having the following physical and chemical properties:

Contains 50% Glycerin (CAS #56-81-5); 49.25% water (CAS #7732-18-5); 0.65% *Commiphora abyssinica* resin extract (CAS #9000-45-7); 0.10% Potassium sorbate (as preservative);
pH: 5.0-7.0;
Density at 20° C.—1.120-1.135;
Refractive index at 20° C.—1.390-1.410;
Water soluble;
Alcohol 50% v/v soluble;
Appearance: translucent solution;
Color: grey orange; and
Odor: characteristic.

In some embodiments the Myrrh tree extract is the commercially available extract Myrrh Milk 1.5PS.

In some embodiments the Myrrh tree extract is the commercially available extract Oleat® of Myrrh UP.

In some embodiments the Myrrh tree extract is *Commiphora abyssinica* resin extract (CAS #9000-45-7).

The Myrrh tree extract may be obtained from one or more parts of the plant as noted above.

In some embodiments the Myrrh tree extract is an extract obtained from the Myrrh tree resin.

In some embodiments the Myrrh tree extract is an extract obtained from the Myrrh tree resin wherein the resin is made from dried tree sap.

In some embodiments the Myrrh tree extract is *Commiphora myrrha* extract.

In some embodiments the Myrrh tree extract is *Commiphora myrrha* resin extract.

In some embodiments the Myrrh tree extract e.g., *Commiphora myrrha* resin extract, is an aqueous extract.

In some embodiments the Myrrh tree extract e.g., *Commiphora myrrha* resin extract, is a water-soluble extract.

In some embodiments the Myrrh tree extract e.g., *Commiphora myrrha* resin extract, is not to be considered as an essential oil.

In some embodiments the Myrrh tree extract e.g., *Commiphora myrrha* resin extract, is not to be considered as a Myrrh oil.

In some embodiments the Myrrh tree extract e.g., *Commiphora myrrha* resin extract, is not an oil extract.

In some embodiments the Myrrh tree extract e.g., *Commiphora myrrha* resin extract, is typically an active fraction having by itself at least one attribute which may be enhanced in a combination with the Dead Sea extract and/or with the *Silybum* extract.

In some embodiments the Myrrh tree extract e.g., *Commiphora myrrha* resin extract, is typically an active fraction having by itself at least one attribute which may be enhanced in a combination with the Dead Sea extract and/or with the Jujube extract.

In some embodiments the concentration of the Myrrh tree extract (e.g., *Commiphora myrrha* resin extract) in the composition/combination (or formulation) of the invention is at least about 0.001% (w/w). At time is it about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%. 0.08%, 0.09%, 0.10%, 0.11%, 0.12%, 0.13%, 0.14%, 0.15%, 0.16%, 0.17%. 0.18%, 0.19%, 0.20%, 0.21%, 0.22%, 0.23%, 0.24%, 0.25%, 0.26%, 0.27%. 0.28%, 0.29%, 0.30%, 0.31%, 0.32%, 0.33%, 0.34%, 0.35%, 0.36%, 0.37%. 0.38%, 0.39%, 0.40%, 0.41%, 0.42%, 0.43%, 0.44%, 0.45%, 0.46%, 0.47%. 0.48%, 0.49%, 0.50%, 0.51%, 0.52%, 0.53%, 0.54%, 0.55%, 0.56%, 0.57%. 0.58%, 0.59%, 0.60%, 0.61%, 0.62%, 0.63%, 0.64%, 0.65%, 0.66%, 0.67%. 0.68%, 0.69%, 0.70%, 0.71%, 0.72%, 0.73%, 0.74%, 0.75%, 0.76%, 0.77%. 0.78%, 0.79%, 0.80%, 0.81%, 0.82%, 0.83%, 0.84%, 0.85%, 0.86%, 0.87%. 0.88%, 0.89%, 0.90%, 0.91%, 0.92%, 0.93%, 0.94%, 0.95%, 0.96%, 0.97%. 0.98%, 0.99%, 1.00%, 1.10%, 1.10%, 1.11%, 1.12%, 1.13%, 1.14%, 1.15%, 1.16%, 1.17%. 1.18%, 1.19%, 1.20%, 1.21%, 1.22%, 1.23%, 1.24%, 1.25%, 1.26%, 1.27%. 1.28%, 1.29%, 1.30%, 1.31%, 1.32%, 1.33%, 1.34%, 1.35%, 1.36%, 1.37%. 1.38%, 1.39%, 1.40%, 1.41%, 1.42%, 1.43%, 1.44%, 1.45%, 1.46%, 1.47%. 1.48%, 1.49%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90% and 5.00% (w/w). Any value which is between any one of the above values is within the scope of the present disclosure.

In some embodiments the concentration of the Myrrh tree extract (e.g., *Commiphora myrrha* resin extract) in the composition (or formulation) of the invention is at between about 0.001% to about 5.00% (w/w), at times between about 0.001% to about 4.50% (w/w), at times between about 0.001% to about 4.00% (w/w), at times between about 0.010% to about 3.50% (w/w), at times between about 0.001% to about 3.00% (w/w), at times between about 0.001% to about 2.50% (w/w), at times between about 0.001% to about 2.00% (w/w), at times between about 0.01% to about 5.00% (w/w), at times between about 0.01% to about 4.50% (w/w), at times between about 0.01% to about 4.00% (w/w), at times between about 0.01% to about 3.50% (w/w), at times between about 0.01% to about 3.00% (w/w), at times between about 0.01% to about 2.50% (w/w), at times between about 0.01% to about 2.00% (w/w), at times between about 0.01% to about 1.50% (w/w), at times between about 0.01% to about 1.00% (w/w), at times between about 0.01% to about 0.50% (w/w), at times between about 0.05% to about 1.50% (w/w), at times between about 0.05% to about 1.00% (w/w), at times between about 0.05% to about 0.50% (w/w), at times between about 0.20% to about 1.50% (w/w), at times between about 0.20% to about 1.00% (w/w), at times between about 0.20% to about 0.50% (w/w), at times between about 0.50% to about 1.50% (w/w), at times between about 0.50% to about 1.00% (w/w), inclusive the end points values.

In some embodiments the concentration of the Myrrh tree extract (e.g., *Commiphora myrrha* resin extract) in the composition (or formulation) of the invention is about 0.001% (w/w), at times about 0.0025, even at times about 0.0030, even at times about 0.0035% (w/w).

In some embodiments the concentration of the Myrrh tree extract (e.g., *Commiphora myrrha* resin extract) in the composition (or formulation) of the invention is about 0.2% (w/w).

In some embodiments the concentration of the Myrrh tree extract (e.g., *Commiphora myrrha* resin extract) in the composition (or formulation) of the invention is about 0.5% (w/w).

In some embodiments the concentration of the Myrrh tree extract (e.g., *Commiphora myrrha* resin extract) in the composition (or formulation) of the invention is about 1.0% (w/w).

In some embodiments the concentration of the Myrrh tree extract (e.g., *Commiphora myrrha* resin extract) in the composition (or formulation) of the invention is about 1.5% (w/w).

The "Jujube" (also known as *Jujuba* or *Ziziphus jujuba*) is a red date, Chinese date. The Chinese Jujube is a species in the genus of *Ziziphus*(some of whose other species are also sometimes referred to as Jujube), in the buckthorn family (Rhamnaceae). It is a small deciduous tree or shrub reaching a height of 5-12 meters, usually with thorny branches. The leaves are shiny-green, ovate-acute, 2-7 centimeters long and 1-3 centimeters wide, with three conspicuous veins at the base, and a finely toothed margin. The flowers are small, 5 mm wide, with five inconspicuous yellowish-green petals. The fruit is an edible oval drupe 1.5-3 centimeters deep; when immature it is smooth-green, with the consistency and taste of an apple with lower acidity, maturing brown to purplish-black, and eventually wrinkled, looking like a small date. There is a single hard kernel, similar to an olive pit, containing two seeds.

The Jujube extract may be obtained commercially. One such commercially available extract is Jujube extract BG-J, See for example [14], of Maruzen Pharmaceutical Co., Ltd., having the following chemical properties:

Contains 47.50% Butylene Glycol (CAS #107-88-0); 47.50% water (CAS #7732-18-5); 5.00% *Ziziphus Jujube* fruit extract (CAS #90045-99-1). This product does not contain anti-oxidants and preservatives.

The Jujube extract may be obtained from one or more parts of the plant as noted above.

In some embodiments the Jujube extract is *Ziziphus jujube* fruit extract (CAS #90045-99-1).

In some embodiments the Jujube extract is a fruit extract.

In some embodiments the Jujube extract is extracted from the fruit of *Zizyphus jujuba* Miller var. inermis Rehder (Rhamnaceae).

In some embodiments the Jujube extract contains vitamin C.

In some embodiments the Jujube extract is an aqueous extract.

In some embodiments the Jujube extract is a water-soluble extract.

In some embodiments the Jujub extract is not to be considered as an essential oil.

In some embodiments the Jujubm extract is not to be considered as Jujub oil.

In some embodiments the Jujub extract is not an oil extract.

In some embodiments the Jujube extract is typically an active fraction having by itself at least one attribute which may be enhanced in a combination with the Dead Sea extract and/or with the Myrrh extract.

In some embodiments the concentration of the Jujube extract in the composition (or formulation) of the invention is at least about 0.01% (w/w). At time is it about 0.01%, 0.02%, 0.03%, 0.04%, 0.05%, 0.06%, 0.07%. 0.08%, 0.09%, 0.10%, 0.11%, 0.12%, 0.13%, 0.14%, 0.15%, 0.16%, 0.17%. 0.18%, 0.19%, 0.20%, 0.21%, 0.22%, 0.23%, 0.24%, 0.25%, 0.26%, 0.27%. 0.28%, 0.29%, 0.30%, 0.31%, 0.32%, 0.33%, 0.34%, 0.35%, 0.36%, 0.37%. 0.38%, 0.39%, 0.40%, 0.41%, 0.42%, 0.43%, 0.44%, 0.45%, 0.46%, 0.47%. 0.48%, 0.49%, 0.50%, 0.51%, 0.52%, 0.53%, 0.54%, 0.55%, 0.56%, 0.57%. 0.58%, 0.59%, 0.60%, 0.61%, 0.62%, 0.63%, 0.64%, 0.65%, 0.66%, 0.67%. 0.68%, 0.69%, 0.70%, 0.71%, 0.72%, 0.73%, 0.74%, 0.75%, 0.76%, 0.77%. 0.78%, 0.79%, 0.80%, 0.81%, 0.82%, 0.83%, 0.84%, 0.85%, 0.86%, 0.87%. 0.88%, 0.89%, 0.90%, 0.91%, 0.92%, 0.93%, 0.94%, 0.95%, 0.96%, 0.97%. 0.98%, 0.99%, 1.00%, 1.10%, 1.10%, 1.11%, 1.12%, 1.13%, 1.14%, 1.15%, 1.16%, 1.17%. 1.18%, 1.19%, 1.20%, 1.21%, 1.22%, 1.23%, 1.24%, 1.25%, 1.26%, 1.27%. 1.28%, 1.29%, 1.30%, 1.31%, 1.32%, 1.33%, 1.34%, 1.35%, 1.36%, 1.37%. 1.38%, 1.39%, 1.40%, 1.41%, 1.42%, 1.43%, 1.44%, 1.45%, 1.46%, 1.47%. 1.48%, 1.49%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90% and 5.00% (w/w). Any value which is between any one of the above values is within the scope of the present disclosure.

In some embodiments the concentration of the Jujube extract in the composition (or formulation) of the invention is at between about 0.01% to about 5.00% (w/w), at times between about 0.01% to about 4.50% (w/w), at times between about 0.01% to about 4.00% (w/w), at times between about 0.01% to about 3.50% (w/w), at times between about 0.01% to about 3.00% (w/w), at times between about 0.01% to about 2.50% (w/w), at times between about 0.01% to about 2.00% (w/w), at times between about 0.01% to about 1.50% (w/w), at times between about 0.01% to about 1.00% (w/w), at times between about 0.01% to about 0.50% (w/w), at times between about 0.05% to about 1.50% (w/w), at times between about 0.05% to about 1.00% (w/w), at times between about 0.05% to about 0.50% (w/w), at times between about 0.20% to about 1.50% (w/w), at times between about 0.20% to about 1.00% (w/w), at times between about 0.20% to about 0.50% (w/w), at times between about 0.50% to about 1.50% (w/w), at times between about 0.50% to about 1.00% (w/w), inclusive the end points values.

In some embodiments the concentration of the Jujube extract in the composition (or formulation) of the invention is about 0.05% (w/w).

In some embodiments the concentration of the Jujube extract in the composition (or formulation) of the invention is about 0.10% (w/w).

In some embodiments the concentration of the Jujube extract in the composition (or formulation) of the invention is about 0.15% (w/w).

In some embodiments the concentration of the Jujube extract in the composition (or formulation) of the invention is about 0.2% (w/w).

In some embodiments the concentration of the Jujube extract in the composition (or formulation) of the invention is about 0.25% (w/w).

In some embodiments the concentration of the Jujube extract in the composition (or formulation) of the invention is about 0.5% (w/w).

In some embodiments the concentration of the Jujube extract in the composition (or formulation) of the invention is about 1.0% (w/w).

In some embodiments the concentration of the Jujube extract in the composition (or formulation) of the invention is about 1.5% (w/w).

In some embodiments, the composition/formulation of the invention comprises at least one Dead Sea extract (e.g., Dead Sea water), at least one Myrrh tree extract (e.g., *Commiphora myrrha* resin extract) and at least one *Silybum* extract (e.g., *Silybum marianum* seeds extract), wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the *Silybum* extract constitutes between about 0.01% to about 1.50% (w/w) of the total weight of the composition.

In some embodiments, the composition/formulation of the invention comprises at least one Dead Sea extract (e.g., Dead Sea water), at least one Myrrh tree extract (e.g., *Commiphora myrrha* resin extract) and at least one *Silybum* extract (e.g., *Silybum marianum* seeds extract), wherein the Dead Sea extract constitutes between about 0.01% to about 2.40% (w/w) of the total weight of the composition, the Myrrh tree extract constitutes between about 0.001% to about 5.00% (w/w) of the total weight of the composition, and the *Silybum* extract constitutes between about 0.01% to about 1.50% (w/w) of the total weight of the composition.

In some embodiments, the composition/formulation of the invention comprises at least one Dead Sea extract (e.g., Dead Sea water), at least one Myrrh tree extract (e.g., *Commiphora myrrha* resin extract) and at least one *Silybum* extract (e.g., *Silybum marianum* seeds extract), wherein the Dead Sea extract constitutes about 0.20% (w/w) of the total weight of the composition, the Myrrh tree extract constitutes about 0.50% (w/w) of the total weight of the composition, and the *Silybum* extract constitutes about 1.00% (w/w) of the total weight of the composition.

In some embodiments, the composition/formulation of the invention comprises at least one Dead Sea extract (e.g., Dead Sea water), at least one Myrrh tree extract (e.g., *Commiphora myrrha* resin extract) and at least one Jujube extract (e.g., *Ziziphus jujube* fruit extract), wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the Jujube extract constitutes between about 0.01% to about 1.50% (w/w) of the total weight of the composition.

In some embodiments, the composition/formulation of the invention comprises at least one Dead Sea extract (e.g., Dead Sea water), at least one Myrrh tree extract (e.g., *Commiphora myrrha* resin extract) and at least one Jujube extract (e.g., *Ziziphus jujube* fruit extract), wherein the Dead Sea extract constitutes between about 0.01% to about 2.40% (w/w) of the total weight of the composition, the Myrrh tree extract constitutes between about 0.001% to about 5.00% (w/w) of the total weight of the composition, and the Jujube extract constitutes between about 0.01% to about 1.50% (w/w) of the total weight of the composition.

In some embodiments, the composition/formulation of the invention comprises at least one Dead Sea extract (e.g., Dead Sea water), at least one Myrrh tree extract (e.g., *Commiphora myrrha* resin extract) and at least one Jujube extract (e.g., *Ziziphus jujube* fruit extract), wherein the Dead Sea extract constitutes about 0.20% (w/w) of the total weight of the composition, the Myrrh tree extract constitutes about 0.50% (w/w) of the total weight of the composition, and the Jujube extract constitutes about 0.50% (w/w) of the total weight of the composition.

As used herein, the expression "active combination" refers to the ability of the combination to exert one or more protective/preventive therapeutic effect (e.g., on the skin) and/or skin care effect, as disclosed herein. In particular, the effect is associated with the capability of the combination to prevent and/or reduce and/or inhibit the glycation of one or more biomolecules, in particular skin biomolecules, and/or the capability of the combination to prevent and/or reduce and/or inhibit the formation of AGEs, in particular skin AGEs. Neither of the components is regarded as a carrier, diluent or excipient.

In some embodiments the at least one Dead Sea extract is typically an active fraction having by itself at least one attribute which may be enhanced in a combination with the at least one Myrrh tree extract.

Without wishing to be bound by theory, in the combinations of the invention the at least one Dead Sea extract may improve the aforementioned effect of the Myrrh tree extract on glycation and/or AGEs formation, wherein the Myrrh tree extract may also beneficially provide the combination with anti-oxidation properties.

Without wishing to be bound by theory, in the combinations of the invention, apart from being by itself an active ingredient that inhibits glycation of biomolecules and/or inhibits the formation of AGEs, the Dead Sea extract may serve as an adjuvant of one or more of the other extracts. For example, the Dead Sea extract may serve as an adjuvant of the *Silybum* extract, to improve the activity of the latter e.g., as an anti-glycation agent and/or as AGEs formation inhibitor and/or as an anti-oxidation agent.

Without wishing to be bound by theory, in the combinations of the invention, apart from being by itself an active ingredient that inhibits the formation of AGEs, the Dead Sea extract may serve as an adjuvant of the Myrrh tree extract, to improve the activity of the latter e.g., as an anti-glycation agent and/or as an anti-oxidation agent.

Without wishing to be bound by theory, in the combinations of the invention, apart from being by itself an active ingredient that inhibits the formation of AGEs, the Dead Sea extract may serve as an adjuvant of the Jujube extract, to improve the activity of the latter.

Without wishing to be bound by theory, in the combinations of the invention, the individual extracts might exhibit a complementary anti-glycation and/or inhibition of AGEs formation effect that is exhibited only when the extracts are simultaneously present in the composition. For example, one or more of the extracts may act via a different mechanism that may be complementary, to thereby inhibit glycation efficiently and/or inhibit the formation of AGEs efficiently.

In some embodiments the at least one Myrrh tree extract is typically an active fraction having by itself at least one attribute which may be enhanced in a combination with the at least one Dead Sea extract.

In some embodiments the at least one Dead Sea extract is typically an active fraction having by itself at least one attribute which may be enhanced in a combination with the at least one Myrrh tree extract and the at least one *Silybum* extract.

In some embodiments the at least one Dead Sea extract is typically an active fraction having by itself at least one attribute which may be enhanced in a combination with the at least one Myrrh tree extract and the at least one Jujube extract.

In some embodiments the at least one Myrrh tree extract is typically an active fraction having by itself at least one attribute which may be enhanced in a combination with the at least one Dead Sea extract and the at least one *Silybum* extract.

In some embodiments the at least one Myrrh tree extract is typically an active fraction having by itself at least one attribute which may be enhanced in a combination with the at least one Dead Sea extract and the at least one Jujube extract.

In some embodiments the at least one *Silybum* extract may be an active fraction having by itself at least one attribute which may be enhanced in a combination with the at least one Dead Sea extract.

In some embodiments the at least one *Silybum* extract may be an active fraction having by itself at least one attribute which may be enhanced in a combination with the at least one Myrrh tree extract.

In some embodiments the at least one *Silybum* extract may be an active fraction having by itself at least one attribute which may be enhanced in a combination with the at least one Dead Sea extract and the at least one Myrrh tree extract.

In some embodiments the at least one Jujube extract may be an active fraction having by itself at least one attribute which may be enhanced in a combination with the at least one Dead Sea extract.

In some embodiments the at least one Jujube extract may be an active fraction having by itself at least one attribute which may be enhanced in a combination with the at least one Myrrh tree extract.

In some embodiments the at least one Jujube extract may be an active fraction having by itself at least one attribute which may be enhanced in a combination with the at least one Dead Sea extract and the at least one Myrrh tree extract.

Without wishing to be bound by theory, at times the at least one *Silybum* extract and the at least one Jujube extract might not be compatibly with each other and/or once present together in the composition with the at least one Dead Sea extract active ingredient and the least one Myrrh tree extract active ingredient. Thus, mutule present of the at least one *Silybum* extract and the at least one Jujube extract may provide unfavorable effect on the compositions ability to inhibit glycation (e.g., protein glycation such as skin protein glycation) and/or inhibit AGEs formation e.g., associated with the glycation inhibition.

Accordingly, in some embodiments the composition of the invention comprises at least one Dead Sea extract and at least one Myrrh tree extract, wherein the composition may further comprise at least one *Silybum* extract or at least one Jujube extract.

In some embodiments the composition of the invention comprises at least one Dead Sea extract and at least one Myrrh tree extract, wherein the composition may further comprise at least one *Silybum* extract and at least one Jujube extract, wherein the at least one *Silybum* extract and the at least one Jujube extract are present in said compositions at concentrations that are beneficial to the anti-glycation and/or AGEs formation inhibition performance of the composition e.g., the concentrations do not negate and/or reduces the anti-glycation and/or AGEs formation inhibition effect observed with the compositions of the invention that comprises the at least one Dead Sea extract, the at least one Myrrh tree extract and any one of the at least one *Silybum* extract and the at least one Jujube extract.

In some embodiments the composition of the invention comprises at least one Dead Sea extract and at least one Myrrh tree extract, wherein the composition further comprises at least one *Silybum* extract. In some embodiments said composition is substantially free (e.g., includes traces amounts) of Jujube extract. In some embodiments said composition is free of Jujube extract.

In some embodiments the composition of the invention comprises at least one Dead Sea extract and at least one Myrrh tree extract, wherein the composition further comprises at least one Jujube extract. In some embodiments said composition is substantially free (e.g., includes traces amounts) of *Silybum* extract. In some embodiments the composition is free of *Silybum* extract.

In another one of its aspects the present invention provides an anti-glycation composition comprising as an active combination at least one Dead Sea extract and at least one Myrrh tree extract.

In some embodiments the anti-glycation composition may further comprise at least one *Silybum* extract and/or at least one Jujube extract.

In some embodiments the anti-glycation composition may further comprise at least one *Silybum* extract or at least one Jujube extract.

In some embodiments the anti-glycation composition may further comprise at least one *Silybum* extract and at least one Jujube extract wherein the at least one *Silybum* extract and the at least one Jujube extract are present in said compositions at concentrations that are beneficial to the anti-glycation performance of the composition e.g., the concentrations do not negate and/or reduces the anti-glycation and/or AGEs formation inhibition effect observed with the compositions of the invention that comprises the at least one Dead Sea extract, the at least one Myrrh tree extract and any one of the at least one *Silybum* extract and the at least one Jujube extract.

In some embodiments the anti-glycation composition comprises as an active combination at least one Dead Sea extract, at least one Myrrh tree extract and at least one *Silybum* extract.

In some embodiments the anti-glycation composition comprises as an active combination at least one Dead Sea extract, at least one Myrrh tree extract and at least one *Silybum* extract, wherein the combination is substantially free of Jujube extract.

In some embodiments the anti-glycation composition comprises as an active combination at least one Dead Sea extract, at least one Myrrh tree extract and at least one *Silybum* extract, wherein said combination is free of Jujube extract.

In some embodiments the anti-glycation composition comprises as an active combination at least one Dead Sea extract, at least one Myrrh tree extract and at least one Jujube extract.

In some embodiments the anti-glycation composition comprises as an active combination at least one Dead Sea extract, at least one Myrrh tree extract and at least one Jujube extract, wherein said combination is substantially free of *Silybum* extract.

In some embodiments the anti-glycation composition comprises as an active combination at least one Dead Sea extract, at least one Myrrh tree extract and at least one Jujube extract, wherein said combination is free of *Silybum* extract.

As used herein the term "glycation" refers to a mechanism that results from attachment of free sugars to biomolecules such as proteins, lipids and nucleic acids. In particular, the term refers to a non-enzymatic one or more chemical reactions of reducing sugar/s with biomolecules (e.g., proteins).

As used herein the term "Advanced Glycation End Products (AGEs)" refers to modified biomolecules such as proteins, lipids and nucleic acids that had passed a non-enzymatic oxidizing glycation process activated by reducing sugars. The term also encompasses irreversible products formed from glycated proteins that rearrange e.g., underwent one or more of dehydration, cyclization, oxidation, or polymerization.

In some embodiments the biomolecule is one or more of at least one protein, at least one lipid and at least one nucleic acid.

In some embodiments the biomolecule is a lipid.

In some embodiments the biomolecule is a nucleic acid.

In some embodiments the biomolecule is a protein e.g., a skin protein.

In some embodiments the protein is at lease one extracellular matrix protein.

In some embodiments the extracellular matrix protein is one or more of collagen (e.g., collagen I), vimentin and elastin.

In some embodiments the extracellular matrix protein is vimentin.

In some embodiments the extracellular matrix protein is elastin.

In some embodiments the extracellular matrix protein is at least one of collagen and elastin.

In some embodiments the AGEs protein is selected from keratin, pentosidine, collagen (e.g., collagen I), vimentin, elastin or any combination thereof.

In some embodiments the AGEs protein is a filamentous protein e.g., keratin.

In some embodiments the AGEs is at lease one protein e.g., a skin protein.

In some embodiments the AGEs is one or more of a carboxymethyl-lysine (CML), a carboxyethyl lysine (CEL), and a fructose-lysine adduct.

In some embodiments the AGEs is a carboxymethyl-lysine (CML).

In some embodiments the AGEs is a carboxyethyl lysine (CEL).

In some embodiments the AGEs is a fructose-lysine adduct.

In some embodiments the AGEs is pentosidine.

In some embodiments the AGEs protein is at lease one extracellular matrix protein.

In some embodiments the AGEs extracellular matrix protein is one or more of collagen (e.g., collagen I), vimentin and elastin.

In some embodiments the AGEs extracellular matrix protein is vimentin.

In some embodiments the AGEs extracellular matrix protein is elastin.

In some embodiments the AGEs extracellular matrix protein is at least one of collagen and elastin.

In some embodiments the AGEs protein is a filamentous protein e.g., keratin.

In some embodiments the compositions of the invention are anti-glycation compositions.

As used herein the term "anti-glycation composition" refers to a composition that comprises an active combination of ingredients that prevents and/or reduces and/or inhibits the glycation of one or more biomolecules e.g., at least one protein, at least one lipid, at least one nucleic acid or any combination thereof. In particular, skin/dermal biomolecules. The anti-glycation composition may also prevent and/or reduce and/or inhibit the formation/generation of AGEs.

As used herein the term "anti-glycation agent" refers to an agent that prevents and/or reduces and/or inhibits the glycation of one or more biomolecules e.g., at least one protein, at least one lipid, at least one nucleic acid or any combination thereof. In particular, skin/dermal biomolecules. The anti-glycation agent may also prevent and/or reduce and/or inhibit the formation/generation of AGEs.

In some embodiments the at least one Dead Sea extract is an anti-glycation ingredient/agent.

In some embodiments the at least one Dead Sea extract is AGEs formation inhibitor.

In some embodiments the at least one Myrrh tree extract is an anti-glycation ingredient/agent.

In some embodiments the at least one Myrrh tree extract is AGEs formation inhibitor.

In some embodiments the at least one *Silybum* extract is an anti-glycation ingredient/agent.

In some embodiments the at least one *Silybum* extract is AGEs formation inhibitor.

In some embodiments the at least one Jujube extract is an anti-glycation ingredient/agent.

In some embodiments the at least one Jujube extract is AGEs formation inhibitor.

In some embodiments the composition of the invention is a synergistic composition comprising as an active combination at least one Dead Sea extract, at least one Myrrh tree extract and at least one *Silybum* extract.

In some embodiments the composition of the invention is a synergistic composition comprising as an active combination at least one Dead Sea extract, at least one Myrrh tree extract and at least one Jujube extract.

In another one of its aspects the present invention provides a composition according to the invention for preventing and/or reducing and/or inhibiting the glycation of one or more biomolecules.

In another one of its aspects the present invention provides a composition according to the invention for use in preventing and/or reducing and/or inhibiting the glycation of one or more biomolecules.

In another one of its aspects the present invention provides a composition according to the invention for use in a method of preventing and/or reducing and/or inhibiting the glycation of one or more biomolecules, the method comprises administrating (e.g., topical application) said composition to a subject.

In a further one of its aspects the present invention provides a composition according to the invention for preventing and/or reducing and/or inhibiting the formation of AGEs.

In a further one of its aspects the present invention provides a composition according to the invention for use in preventing and/or reducing and/or inhibiting the formation of AGEs.

In a further one of its aspects the present invention provides a composition according to the invention for use in a method of preventing and/or reducing and/or inhibiting the formation of AGEs, the method comprises administrating (e.g., topical application) said composition to a subject.

In another one of its aspects the present invention provides a composition according to the invention for preventing and/or reducing and/or inhibiting the glycation of one or more biomolecules, and/or for preventing and/or reducing and/or inhibiting the formation of AGEs.

In another one of its aspects the present invention provides a composition according to the invention for use in preventing and/or reducing and/or inhibiting the glycation of one or more biomolecules and/or preventing and/or reducing and/or inhibiting the formation of AGEs.

In another one of its aspects the present invention provides a composition according to the invention for use in a method of preventing and/or reducing and/or inhibiting the glycation of one or more biomolecules and/or preventing and/or reducing and/or inhibiting the formation of AGEs, the method comprises administrating (e.g., topical application) said composition to a subject.

In some embodiments the compositions of the invention are for preventing and/or reducing and/or inhibiting the glycation of lysine residues of at least one protein (e.g., a skin protein) in a subject (e.g., a human subject).

In some embodiments the compositions of the invention are for preventing and/or reducing and/or inhibiting the glycation of at least one protein (e.g., a skin protein) and for preventing and/or reducing and/or inhibiting the formation of AGEs of at least one protein.

Yet, in a further one of its aspects the present invention provides a method of preventing and/or reducing and/or inhibiting the glycation of one or more biomolecules, the method comprising topical application of a composition according to the invention onto at least a region of the skin of a subject.

In another one of its aspects the present invention provides a method of preventing and/or reducing and/or inhibiting the formation of AGEs, the method comprising topical application of a composition according to the invention onto at least a region of the skin of a subject.

In another one of its aspects the present invention provides a method of preventing and/or reducing and/or inhibiting the glycation of one or more biomolecules and for preventing and/or reducing and/or inhibiting the formation of AGEs, the method comprising topical application of a composition according to the invention onto at least a region of the skin of a subject.

Yet, in a further one of its aspects the present invention provides a method of increasing the effectiveness of a composition comprising at least one *Silybum* extract which is capable of preventing and/or reducing and/or inhibiting the glycation of one or more biomolecules, and/or preventing and/or reducing and/or inhibiting the formation of AGEs in the skin of a subject (e.g., a human subject), the method comprising including in the composition at least one Dead Sea extract and at least one Myrrh extract, thereby arriving at the compositions disclosed herein.

In a further one of its aspects the present invention provides a method of increasing the effectiveness of a composition comprising at least one Myrrh extract which is capable of preventing and/or reducing and/or inhibiting the glycation of one or more biomolecules, and/or preventing and/or reducing and/or inhibiting the formation of AGEs in the skin of a subject (e.g., a human subject), the method comprising including in the composition at least one Dead Sea extract and optionally at least one *Silybum* extract, thereby arriving at the compositions disclosed herein.

In a further one of its aspects the present invention provides a method of increasing the effectiveness of a composition comprising at least one Myrrh extract and at least one *Silybum* extract, the composition is capable of preventing and/or reducing and/or inhibiting the glycation of one or more biomolecules, and/or preventing and/or reducing and/or inhibiting the formation of AGEs in the skin of a subject (e.g., a human subject), the method comprising including in the composition at least one Dead Sea extract, thereby arriving at the compositions disclosed herein.

In a further one of its aspects the present invention provides a use of the composition according to the invention for the manufacture of a formulation for preventing and/or reducing and/or inhibiting the glycation of one or more biomolecules, and/or for preventing and/or reducing and/or inhibiting the formation of AGEs.

In a further one of its aspects the present invention provides a use of the composition according to the invention for the manufacture of a formulation for preventing and/or reducing and/or inhibiting the glycation of one or more biomolecules.

In a further one of its aspects the present invention provides a use of the composition according to the invention for the manufacture of a formulation for preventing and/or reducing and/or inhibiting the formation of AGEs.

In a further one of its aspects the present invention provides a use of the composition according to the invention for preventing and/or reducing and/or inhibiting the glycation of one or more biomolecules and preventing and/or reducing and/or inhibiting the formation of AGEs.

In a further one of its aspects the present invention provides a use of the composition according to the invention for preventing and/or reducing and/or inhibiting the glycation of one or more biomolecules.

In a further one of its aspects the present invention provides a use of the composition according to the invention for preventing and/or reducing and/or inhibiting the formation of AGEs.

It is noted that the amount of any one the Dead Sea extract and the plant extracts i.e., Myrrh tree extract, *Silybum* extract and Jujube extract necessary to bring about the aforementioned effects of the compositions/formulations/combinations of the present invention on glycation and/or formation of AGEs (e.g., preventing and/or reducing and/or inhibiting the glycation of one or more biomolecules and/or preventing and/or reducing and/or inhibiting the formation of AGEs) is not fixed per-se, and might be dependent upon the user's skin type and, where present, the severity and extent of the patient's skin condition. Generally, the extracts contained in the composition/formulation of the invention are topically applied in effective amounts to skin areas such as aged skin areas or skin areas susceptible to damage because of glycation and/or AGEs.

Without wishing to be bound by theory, by combining the two or more extracts of the present invention i.e., the Dead Sea extract, the Myrrh tree extract, and *Silybum* extract or Jujube extract, there might be a decrease in their toxicity profiles or the potential of a skin irritation in sensitive individuals. An enhanced efficacy of the aforementioned effect of the compositions on glycation and/or formation of AGEs when the extracts are administered in combination may also occur. A composition/formulation (e.g., topical composition/formulation) comprising the aforementioned two or more extracts is advantages compared to a composition having only a single extract, for example, since the extracts might work in different ways (e.g., by inhibiting the pathway to AGEs at different stages) there might be an enhanced effect when the extracts are combined compared to the use of a single extract. Therefore, the combinations of the invention are beneficial for use e.g., on the skin, to relieve the effects of damage from glycation (e.g., of skin proteins) and formation of AGEs.

For example, the inventors of the present invention illustrated that both Dead Sea extract and Myrrh tree extracts are inhibitors of AGE. Thus, the combination of these extracts provides AGE inhibition effect using lower concentrations of the extracts than would be required if single extracts were used. As noted, the reduced concentrations of the aforementioned extracts might decrease any toxicity effects of these extracts and their potential of irritating skin in sensitive individuals. The combination of these two extracts with *Silybum* extract and/or Jujube extract is similarly advantageous e.g., for the reasons detailed herein above and below.

Further, the Dead Sea extract and the plant extracts described herein incorporated in the compositions/formulation of the invention provide other benefits as well. For example, the Myrrh tree extract and the *Silybum* extract illustrated anti-oxidation attributes. The Dead Sea extract is known for its therapeutical attributes (See e.g., [10]). Combinations of these extracts beneficially illustrate both attributes. Therefore, a composition/formulation comprising a combination of the extracts (e.g., Dead Sea extract, Myrrh tree extract and *Silybum* extract; and Dead Sea extract, Myrrh tree extract and Jujube extract) are advantageous over a composition/formulation comprising only one of these extracts.

The compositions/formulations of the invention having a combination of the extracts disclosed herein e.g., the Dead Sea extract, the Myrrh tree extract, and the *Silybum* extract or Jujube extract, are particularly useful in a topical formulation when the skin and underlying tissue or the composition/formulation contain high concentrations of substances such as saccharides, vitamin C, amino acids prone to glycation, and the like. Such substances may have skin benefits as functional ingredients (e.g., sugars as humectants, sugar derived emulsifiers or surfactants) or actives (ascorbate, amino acids). The combinations of the invention might eliminate or decrease the potential anti-glycation effects of these substances allowing these substances to illustrate their beneficial effect. For example, vitamin C is widely used in topical formulations. It is an easily oxidizable compound. Its oxidized form is dehydroascorbate, a species which leads to the formation of AGEs. Therefore, the present invention is particularly useful in combination with topical formulations containing vitamin C. Therefore, the formulations/compositions of the invention are particularly useful when the skin, underlying tissue, the administered formulation (either in the same formulation of the invention or in a separate other formulation) or a combination thereof contains a high concentration of agents prone to glycation or agents whose oxidation product are prone to glycation or agents included for other beneficial properties that are themselves glycating agents.

The compositions/formulations of the invention may inhibit the formation of AGEs by reducing the AGEs concentration in the skin by at least 10%, at times at least 20%, at times by at least 30%, at times 40% or even at times by at least 50%. The concentration of the AGEs in the skin may be measured by means known in the art. Non limiting example is by non-invasive autofluorescence reader that can be used to measure the fluorescence exhibited by AGEs. The measurement may be performed in one measurement regimen e.g., after one week of treatment, e.g., topical application of at least once daily. Further measurements may follow e.g., after two, at times three, at times four or more weeks of treatment.

In some embodiments the compositions/formulations of the invention my inhibit the formation of AGEs to an extent greater than 10%, at times at least 20%, at times by at least 30%, at times 40% or even at times by at least 50% compared to a control composition/formulation e.g., not containing the active extracts of the invention.

At times, the compositions of the invention significantly prevent and/or reduce and/or inhibit glycation and/or formation of AGEs. In this respect, term significantly denotes an effect which is statistically significant and will usually be a prevention/reduction/inhibition by least about 20%, e.g., by least about 40%, by least about 50%, by least about 70% or by least about 90% in comparison to an untreated subject or to a subject treated with a control composition/formulation e.g., not containing the active extracts of the invention. The conditions under which the comparison is carried out may be physiological conditions or non-physiological conditions such as, e.g., an elevated temperature (i.e., a temperature above body temperature). The period over which the comparison is to be carried out depends on the effect to be measured and the conditions employed and may, for example, be about 24 hours, about one week, about one month or even longer.

Yet, in a further one of its aspects the present invention provides a composition according to the invention for preventing and/or treating at least one disease or disorder of the skin of a subject, said disease or disorder being associate with and/or being induced by glycation of one or more biomolecules and/or by formation of AGEs.

In a further one of its aspects the present invention provides a use of the composition according to the invention for the manufacture of a formulation for preventing and/or treating at least one disease or disorder of the skin of a subject, said disease or disorder being associate with and/or being induced by glycation of one or more biomolecules and/or by formation of AGEs.

In a further one of its aspects the present invention provides a method for treating and/or preventing at least one disease or disorder of the skin of a subject, wherein the disease or disorder being associate with and/or being induced by glycation of one or more biomolecules and/or formation of AGEs, the method comprises topical application of the composition (or any formulation thereof) according to the invention onto (at least a region of) the skin of the subject in need thereof.

In another one of its aspects the present invention provides a method for protecting and/or improving the state of (at least a region of) the skin of a subject, preventing and/or treating imperfections of (at least a region of) the skin of a subject in need thereof, the method comprises topical application of the composition (or any formulation thereof) according to the invention onto (at least a region of) the skin of the subject in need thereof, wherein the protecting and/or improving the state of the skin of a subject, preventing and/or treating imperfections of the skin of a subject in need thereof being associated with the composition capability of preventing and/or reducing and/or inhibiting the glycation of one or more biomolecules, and/or the composition capability of preventing and/or reducing and/or inhibiting the formation of AGEs.

In a further one of its aspects the present invention provides a method of substantially preventing or delaying the onset of, or substantially preventing or retarding the progression of a condition/disorder/disease which is associated with the formation of AGEs in a subject (e.g., a human) in need thereof, the method comprises administering (e.g., topically) to the subject a composition according to the invention.

Non-limiting examples of condition/disorder/disease associated with and/or being induced by glycation of one or more biomolecules and/or by formation of AGEs are one or more of skin wrinkles, skin fine-lines, skin elasticity, skin sagging, skin firmness, skin plumping, skin smoothness, skin roughness, skin pigmentation, un-even skin tone, skin photo-aging, skin appearance, skin detoxification or any combination thereof.

The compositions of the present invention may be made into a wide variety of product forms suitable for, e.g., topical administration onto the skin of a subject.

Thus, in another one of its aspects, the present invention provides a serum, a lotion, an ointment, a gel, a shampoo, a moisturizer, a sunscreen, a cream, a stick, a spray, an aerosol, foam, a paste, a mousse, a solid, semi-solid, or a liquid make-up, a foundation, or a make-up comprising the composition according to the invention.

In another one of its aspects, the present invention provides a serum, a lotion, an ointment, a gel, a moisturizer, a sunscreen, a cream, a stick, a spray, an aerosol, foam, a paste, a mousse, a liquid make-up, a foundation, or a make-up comprising the composition according to the invention.

In some embodiments the liquid may be applied onto the skin as a moisturizer.

In some embodiments, the composition of the invention is formulated as a lotion.

In some embodiments, the composition of the invention is formulated as an emulsion.

In some embodiments, the composition of the invention is formulated as a facial formulation.

In some embodiments, the composition of the invention is formulated as a body formulation.

In some embodiments, the composition of the invention is formulated as a leave on formulation.

In some embodiments, the composition of the invention is formulated as rinse off formulation.

As used herein, a "leave on" (in contrary to "rinse off") composition/formulation refers to a composition/formulation that may be in prolonged contact with the skin and can be applied to a skin region without the need to remove it from the skin (e.g., by wiping or rinsing it off) in any way.

In some embodiments, the leave-on composition/formulation may be adapted to be applied to a skin region and to be left on the skin for a time sufficient to achieve an end result.

In another one of its aspects, the present invention provides a use of the composition according to the invention for the preparation of a composition/formulation, the composition/formulation being selected from a cosmetic, skin-care, dermatological or a pharmaceutical composition/formulation.

In some embodiments the compositions/formulations of the invention are anti-aging compositions.

The term "aging" may be envisaged as one or more of changes experienced by the skin with age (chrono-aging), through exposure to the sun (photo-aging) and to environmental agents (such as tobacco smoke, extreme climatic conditions of cold, heat, or wind, chemical contaminants or pollutants). The term may also encompass one or more of external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, sagging of the skin such as sagging cheeks, the appearance of bags under the eyes or the appearance of a double chin, among others, changes to the color of the skin such as marks, reddening, bags under the eyes or the appearance of hyperpigmented areas such as age spots or freckles among others, anomalous differentiation, elastosis, orange-peel skin, loss of collagen structure and other histological changes of the stratum corneum, of the dermis, epidermis, vascular system (for example the appearance of spider veins or telangiectasias) or of those tissues close to the skin, among others.

The term "photoaging" may refer to a set of processes due to the prolonged exposure of the skin to ultraviolet radiation which result in the premature aging of the skin, and present the same physical characteristics as aging, such as and not restricted to, flaccidity, sagging, and changes to the color or irregularities in the pigmentation.

The changes of the skin due to aging (e.g. chrono-aging, photoaging and/or environmental aging) may also be referred to as the symptoms or signs of skin aging.

In some embodiments the symptoms or signs of skin aging are resulted from skin glycation and/or from skin AGEs formation.

In some embodiments the symptoms or signs of skin aging are resulted from skin glycation.

In some embodiments the symptoms or signs of skin aging are resulted from skin AGEs formation.

In some embodiments aging refers to changes experienced by the skin with age (chrono-aging).

In some embodiments aging refers to changes experienced by the skin through exposure to the sun (photo-aging).

In some embodiments aging refers to changes experienced by the skin through exposure to environmental agents.

In some embodiments the compositions/formulations of the present invention may be used to prevent or combat symptoms or signs of skin aging e.g., such as those detailed herein. For example, prevent and/or combat the reduction in elastic and plastic properties of tissues, particularly of the skin.

Non-limiting examples of skin disorders/conditions that my be prevented or improved e.g., by topical application of the compositions/formulations of the present disclosure, are one or more of skin wrinkles, skin fine-lines, skin elasticity, skin sagging, skin firmness, skin plumping, skin smoothness, skin roughness, skin pigmentation, un-even skin tone, skin photo-aging, skin appearance, skin de toxification or any combination thereof.

In some embodiments the skin condition is a non-medical condition e.g., associated with normal skin conditions.

In some embodiments the skin condition is a medical condition e.g., associate with pathological skin conditions.

In some embodiments the disease and/or disorder disclosed herein is a non-medical condition e.g., associated with normal skin conditions.

In some embodiments the disease and/or disorder disclosed herein is a medical condition e.g., associate with pathological skin conditions.

In some embodiments the methods disclosed herein are non-therapeutic methods e.g., associated with normal skin conditions.

In some embodiments the methods disclosed herein are therapeutic methods e.g., associate with pathological skin conditions.

In some embodiments the compositions/formulations of the invention are cosmetic compositions/formulations.

In some embodiments the compositions/formulations of the invention are therapeutic compositions/formulations e.g., pharmaceutical compositions/formulations.

In some embodiments, the compositions are topical compositions e.g., cosmetic topical compositions or topical pharmaceutical compositions.

In another one of its aspects the present invention provides compositions for use as herein described and exemplified.

The compositions according to the invention (cosmetic or therapeutic) may comprise at least one dermatological, cosmetically or pharmaceutically acceptable additive selected amongst inert and effect-inducing additives. In some embodiments, the inert additive is selected from a diluent, a preservative, an abrasive, an anti-caking agent, an antistatic agent, a binder, a buffer, a dispersant, an emollient, an emulsifier, a co-emulsifiers, a fibrous material, a film forming agent, a fixative, a foaming agent, a foam stabilizer, a foam booster, a gallant, a lubricant, a moisture barrier agent, an opacifier (e.g., styrene/acrylamide copolymer), a plasticizer, a preservative, a propellant, a stabilizer, a surfactant, a suspending agent, a thickener, a wetting agent, and a liquefier.

In some embodiments, the at least one inert additive is a smoothness enhancer ingredient, such as silica.

In some embodiments, each of the at least one dermatological, cosmetically or pharmaceutically acceptable additives may constitute between about 0.05% to 15% (w/w/) of the total weight of the formulation. In some embodiments, the at least one additive constitutes between 0.05% and 10% or between 0.05% and 8%, or between 0.05% and 7%, or between 0.05% and 6%, or between 0.05% and 5% of the total weight of the formulation.

In some embodiments, the at least one inert additive is a diluent being selected from water, Bisabolol, propane diol, propylene glycol, butylene glycol, glycerin, safflower oil and mixtures thereof.

In some embodiments, the at least one inert additive is a preservative being selected from one or more of methylparaben, methyldibromo glutaronitrile, phenethyl alcohol, glyceryl caprilate, propylparaben, methylisothiazolinone, decylene glycol, dehydroacetic acid, phenoxyethanol, benzoic acid, 2-methyl-2H-isothiazoline-3-one, polyethylene glycol monococoate, polyethylene glycol dicocoate, polyethylene Glycol, iodopropynyl butylcarbamate, 1.2-hexanediol, caprylyl glycol, imidazolidinyl urea, DMDM Hydantoin, Ipbc, MIT, 2,3-bronopol.

In further embodiments, the inert additive is an emulsifier being selected from one or more of cetyl hydroxyethylcellulose, cetyl alcohol, ceteth-20 (a polyethylene glycol derivative of cetyl alcohol), cetearyl olivate, cetyl palmitate, sorbitan olivate, sorbitan palmitate, stearates, steareth-20 (polyethylene glycol ethers of stearic acid—octadecyl polyoxyethylene ether), steareth-25.

In some embodiments, the stearate is selected from PEG-40 stearate, glyceryl steatrate, sorbitan tristearate, stearyl alcohol and mixtures thereof.

In some embodiments, the stearate is glyceryl stearate.

In still other embodiments, the inert additive is an emollient, being selected from vegetable and animal fats and oils such as castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, chamomilla recutita (matricaria) flower oil, hypericum perforatum oil, soybean oil and *Vitis vinifera* (grape) seed oil; acetoglyceride esters, such as acetylated monoglycerides; alkyl esters of fatty acids having 10 to 24 carbon atoms which include, but are not limited to, methyl, isopropyl, and butyl esters of fatty acids such as hexyl laurate, isohexyl laurate, ethylhexyl palmitate, isohexyl palmitate, isopropyl palmitate, octyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, bydrogenolysis of lanolin, ethoxylated sorbitol lanolin, and liquid and semisolid lanolin absorption bases; polyhydric alcohol esters such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; Wax esters such as beeswax, spermaceti, myristyl myristate, stearyl stearate; forming a mixture of ether esters; vegetable waxes including, but not limited to, carnauba and candelilla waxes; surface active silicone derivatives such as cyclopentasiloxane PEG/PPG-18/18 dimethicone, dimethicone, dimethicone crosspolymer, cyclomethicone, cyclomethicone&dimethiconol; caprylic/capric triglyceride; and cholesterol fatty acid esters and any mixtures thereof.

In some embodiments, each of the at least one inert additive may constitute between about 0.05% to 15% (w/w) of the total weight of the formulation. In some embodiments, the at least one inert additive constitutes between 0.05% and 10% or between 0.05% and 8%, or between 0.05% and 7%, or between 0.05% and 6%, or between 0.05% and 5% of the total weight of the formulation.

In other embodiments, the effect-inducing additive is selected from an anti-acne agent, an anti-aging agent, an antibacterial agent, an anti-cellulites agent, agent, an antifungal agent, an anti-inflammatory agent, an anti-irritation agent (e.g., allantoin, Aloe Barbadensis leaf juice), an antimicrobial agent, an antioxidant (e.g., butylated hydroxyanisole, propyl gallate, an antiperspirant agent, an antiseptic agent, a cell stimulant, a cleansing agent, a conditioner, a deodorant, a fragrance ingredient (e.g., perfume, limonene), a depilatory, a detergent, an enzyme, an essential oil, an exfoliant, a fungicide, a glosser, a humectants (e.g., Erythritol, Homarine HCl, Ceratonia Siliqua (carob bean) gum), a moisturizer (e.g., sodium hyaluronate), an ointment base, a perfume, a protein, a skin calming agent, a skin cleanser, a skin conditioner (skin conditioning agent), a skin healing agent, a skin lightening agent, a skin protectant, a skin smoothing agent, a skin softening agent, a skin soothing agent, a sunscreen agent, a tanning accelerator, vitamins, a colorant, and a flavoring agent.

In some embodiments, the at least one additive is a sunscreen, such as Ethyl hexyl methoxycinnamate or titanium dioxide.

In some embodiments, each of the at least one effect-inducing additive may constitute between about 0.05% to 15% (w/w) of the total weight of the formulation. In some embodiments, the at least one inert additive constitutes between 0.05% and 10% or between 0.05% and 8%, or between 0.05% and 7%, or between 0.05% and 6%, or between 0.05% and 5% of the total weight of the formulation.

The cosmetic or pharmaceutical compositions of the invention may also comprise pharmaceutical actives useful in the form of a chemical substance, material or compound, e.g., suitable for topical administration, to induce a desired local or systemic effect. Non-limiting examples of such actives are an antibiotic, an antiviral agent, an analgesic (e.g. ibuprofen, acetyl salicylic acid, naproxen, and the like), an antihistamine, an anti-inflammatory agent, an antipruritic, an antipyretic, an anesthetic agent, a diagnostic agent, a hormone, an antifungal agent, an antimicrobial agent, a cutaneous growth enhancer, a pigment modulator, an antiproliferative, an antipsoriatic, a retinoid, an anti-acne medicament (e.g. benzoyl peroxide, sulfur, and the like), an antineoplastic agent, a phototherapeutic agent, a keratolys (e.g. resorcinol, salicylic acid, and the like) and mixtures thereof.

Application of a composition of the invention onto the skin of a subject, for cosmetic/skin-care or therapeutic purposes may be in a single dose, in multiple doses, in a continuous or intermittent manner, depending, for example, upon the subject's physiological condition, whether the purpose of the administration is cosmetic or therapeutic/prophylactic and other factors known to the medical practitioner. The application of a composition of the invention may be essentially continuous over a pre-selected period of time or may be in a series of spaced doses.

The compositions of the invention are typically prepared by combining the ingredients of the active combination in appropriate concentrations. Other active or inert additives selected by one of skill in the art may optionally be added. The absolute weight of a given active agent included in a unit dose can vary widely. For example, about 0.1 microgram to about 5 g, or about 1 microgram to about 1 g, or about 10 micrograms to about 500 mg, of at least one of the components can be administered by topical administration.

The compositions of the invention, being substantially for topical use, may be a skin-care formulation or a therapeutic formulation.

In some embodiments, the compositions of the invention are skin-care or dermo-pharmaceutical compositions (including, e.g., toiletries, health and beauty aids and cosmeceuticals) used for cosmetic and personal skin-care applications.

The term "cosmetic composition" or "skin care composition" relates to a composition of the invention that can be used for cosmetic purposes, purposes of hygiene or skin-care or as a basis for delivery of one or more pharmaceutical ingredients. It is also possible that these compositions are used for two or more of these same purposes at one time. For example, a medicated cleaner may be used as a personal care product, i.e., to provide clean skin, and at the same time have pharmacological properties.

In some embodiments, the cosmetic compositions are for promoting bodily attractiveness, cover or mask the physical manifestations of a disorder, disease or condition, modulate or alleviate wrinkling, unevenness and dryness in the skin of a mammal. The compositions additionally regulate skin condition and signs of skin aging (all perceptible manifestations as well as any other macro or micro effects) by regulating visible and/or tactile discontinuities in skin texture, including fine lines, wrinkles, enlarged pores, roughness and other skin texture discontinuities associated with aged skin with reduced irritation and dryness.

In some embodiments the compositions of the invention are substantially devoid/free of petrolatum (i.e., a semisolid mixture of long chain, greater than C=20 hydrocarbons) e.g., such as that disclosed in [15] U.S. Pat. No. 10,722,461, the content of which is incorporated herein by reference.

In some embodiments the compositions of the invention are substantially devoid/free of petrolatum matrix e.g., such as that disclosed in [15] U.S. Pat. No. 10,722,461, the content of which is incorporated herein by reference.

In some embodiments the compositions of the invention may comprise less the 20% petrolatum, at times less than 19, 18, 17, 16, 15, 14, 13, 12, 11, 10, 11, 10, 9, 8, 7, 6, 5, 4, 3, 2, 1, 0.9, 0.8, 0.7, 0.6, 0.5, 0.4, 0.3, 0.2 or less than 0.1% petrolatum.

In some embodiments the compositions/formulations of the invention comprise at least 10% (w/w) water.

In some embodiments the compositions/formulations of the invention are aqueous compositions/formulations e.g., comprises at least 51% (w/w) water.

In some embodiments the compositions/formulations of the invention are liquid at room temperature.

In some embodiments the compositions/formulations of the invention comprise at least one emulsifier.

In some embodiments the skin of the subject is a healthy non-wounded skin.

In some embodiments the skin is not a wound skin site e.g., at any stage of healing. Non limiting examples of such site as those disclosed in [15] U.S. Pat. No. 10,722,461, for example: an abrasion, abscess, an arterial ulcer, a burn, debridement, a diabetic ulcer, dry or dotted blood, epithelial tissue, gangrene, a lesion, maceration, necrosis, rash, surgical incisions.

In some embodiments the active ingredients of the compositions/formulations of the invention constitute together more than 1% (w/w).

In some embodiments the active ingredients of the compositions/formulations of the invention are dissolved in the composition/formulation.

In some embodiments the active ingredients of the compositions/formulations of the invention are water soluble.

In some embodiments the compositions/formulations of the invention are free of active ingredients aggregates.

In some embodiments the compositions/formulations of the invention are homogenous continuous single-phase compositions/formulations.

In some embodiments the compositions/formulations of the invention are emulsion free.

In some embodiments the compositions of the invention are substantially devoid/free of non-natural or synthetic nitrone derivatives.

In some embodiments the compositions of the invention are substantially devoid/free of nitrone derivatives e.g., such as those disclosed in [16] US 2007/0203240, the content of which is incorporated herein by reference. The derivatives are also referred to as spin traps. Exemplary nitrone derivatives (or "spin traps") include α-phenyl butyl nitrone (PBN), PBN doxylcyclohexane radicals, 5,5-dimethyl pyrroline N-oxide (DMPO), α-(4-pyridyl 1-oxide)-N-tert-butylnitrone (POBN), 2,2,6,6-tetramethylpiperidine 1-oxide, 4-hydroxytetramethylpiperidine 1-oxide, and the salts of N-(1-oxido-2,2,6,6-tetramethyl-4-piperidyl)-N,N-dimethyl-N-hydroxyethylammonium, 3,5-dibromo-4-nitroobenzenesulfonic acid, 2-methyl-2-nitrosopropane, nitrosodisulfonic acid, α-(4-pyridyl-1-oxide)-N-t-butylnitrone, 3,3,5,5-tetramethylpyrroline N-oxide, and 2,4,6-tri-t-butylnitrosobenzene, or spin-trapping derivatives thereof, or mixtures thereof.

In some embodiments the compositions/formulations of the invention are substantially devoid/free of a ferment extract from a strain of *Eupenicillium crustaceum* species e.g., such as that disclosed in [17] U.S. Pat. No. 10,512,603, the content of which is incorporated herein by reference.

In some embodiments the compositions/formulations of the invention are substantially devoid/free of *Silybum* (Milk thistle) oil e.g., such as that disclosed in [18] RU 2253433 C2, the content of which is incorporated herein by reference.

In some embodiments the compositions/formulations of the invention are substantially devoid/free of biologically active substances of animal origin e.g., such as that disclosed in [18] RU 2253433 C2.

In some embodiments the compositions/formulations of the invention are substantially devoid/free of a lipid soluble compound e.g., such as that disclosed in [19] EP 1 074 245, the content of which is incorporated herein by reference.

In some embodiments the Dead Sea salts and minerals from the Dead Sea extract which are comprised in the compositions/formulations of the invention are not in present a granular form.

In some embodiments the Dead Sea extract constitutes less than 5% of the compositions/formulations of the invention.

In some embodiments the compositions/formulations of the invention are substantially devoid/free of anti-OX40L antibody e.g., such as that disclosed in [20] US 2006/0002929, the content of which is incorporated herein by reference.

In some embodiments the compositions/formulations of the invention are substantially devoid/free of IL-1 antagonist e.g., IL-1 receptor and IL-1RAcP such as those disclosed in [21] US 2003/0049255, the content of which is incorporated herein by reference.

In some embodiments the compositions/formulations of the invention are substantially devoid/free of thick licorice extract such as those disclosed in [22] EA 033620, the content of which is incorporated herein by reference.

In some embodiments the *Silybum* extract constitutes less than 5% of the compositions/formulations of the invention.

In some embodiments the compositions/formulations of the invention are substantially devoid/free of hydrogen peroxide, See [23] US 2003/007939.

In some embodiments the Myrrh extract constitutes less than 1% of the compositions/formulations of the invention.

In some embodiments the Myrrh extract constitutes less than 3% of the compositions/formulations of the invention.

In some embodiments the compositions/formulations of the invention are substantially devoid/free of a fruit extract from pomegranate e.g., such as that disclosed in [24] U.S. Pat. No. 6,800,292, the content of which is incorporated herein by reference.

In some embodiments the compositions/formulations of the invention are substantially devoid/free of phenoxyethanol e.g., such as that disclosed in [25] US 2009/093440, the content of which is incorporated herein by reference.

In some embodiments the compositions/formulations of the invention are substantially devoid/free of one or more of ferulic acid, caffeic acid, tannic acid and ellagic acid e.g., such as those disclosed in [26] WO 2002/069963, the content of which is incorporated herein by reference.

In some embodiments the compositions/formulations of the invention are substantially devoid/free of ultra fine Dead Sea minerals and/or salts e.g., such as those disclosed in [9] U.S. Pat. No. 6,871,805, the content of which is incorporated herein by reference. In some embodiments the compositions/formulations of the invention are substantially devoid/free of non-natural ultra fine Dead Sea minerals and/or salts.

In some embodiments the compositions/formulations of the invention are substantially devoid/free of non-natural ultra fine Dead Sea minerals. In some embodiments the compositions/formulations of the invention are substantially devoid/free of non-natural ultra fine Dead Sea salts. In some embodiments the Dead Sea extract is not one that the minerals thereof were forced through a conical screen mill. In some embodiments the Dead Sea extract comprises native Dead Sea salts and/or minerals e.g., not subjected to milling forces.

In some embodiments the compositions/formulations of the invention are substantially devoid/free of Myrrh oil e.g., such as that disclosed in [9] U.S. Pat. No. 6,871,805.

In some embodiments the compositions/formulations of the invention are substantially devoid/free of essential oil blend e.g., such as that disclosed in [9] U.S. Pat. No. 6,871,805. In some embodiments said essential oil blend includes rosewood, lavender, chamomile, and calendula. In some embodiments said essential oil blend includes biblical scent combination of lavender, hyssop, frankincense, gabanum, and Myrrh. In some embodiments said essential oil blend includes biblical scent combination of lavender, hyssop, frankincense, and gabanum. In some embodiments, in the compositions/formulations of the invention the Myrrh extract does not form part of said essential oils. In some embodiments, the Myrrh extract of the invention does not form part of said essential oils.

In some embodiments the compositions/formulations of the invention are substantially devoid/free of silicon polymers e.g., such as those disclosed in [27] US 2008/0044373, the content of which is incorporated herein by reference. In some embodiments the silicon polymer comprises at least one unit comprising: (1) polyorganosiloxanes comprising at least two groups capable of establishing hydrogen interactions, these two groups being in the polymer chain, and/or (2) polyorganosiloxanes comprising at least two groups capable of establishing hydrogen interactions, these two groups being on grafts or branches.

In some embodiments the compositions/formulations of the invention are substantially devoid/free of one or more anti-glycation agents disclosed in [27] US 2008/0044373, the content of which is incorporated herein by reference. In some embodiments said anti-glycation agent may be hydrophilic or lipophilic agent. In some embodiments said anti-glycation agent are extracts of plants from the Ericacea family, such as an extract of blueberry (*Vaccinium angustifolium*), for example the product sold under the name Blueberry Herbasol Extract PG by the company Cosmetochem. ergothioneine and derivatives thereof and hydroxystilbenes and derivatives thereof such as resveratrol and 3,3',5,5'-tetrahydroxystilbene or any combination thereof. In some embodiments the compositions/formulations of the invention are substantially devoid/free of one or more anti-glycation agents selected from arginine and lysine polypeptides. In some embodiments the compositions/formulations of the invention are substantially devoid/free of the anti-glycation agent blueberry extract.

In some embodiments the compositions/formulations of the invention are substantially devoid/free of ximenynic acid or an oil comprising same such as those disclosed in [28] US 2020/0214955, the content of which is incorporated herein by reference.

In some embodiments the compositions/formulations of the invention are substantially devoid/free of an extract of *Momordica grosvenori* fruit e.g., such as that disclosed in [29] U.S. Pat. No. 10,842,733, the content of which is incorporated herein by reference.

In some embodiments the compositions/formulations of the invention are substantially devoid/free of cellulose ether e.g., such as that disclosed in [30] JP 2002370963, the content of which is incorporated herein by reference.

In some embodiments the compositions/formulations of the invention are substantially devoid/free of a water-soluble component obtained by hydrolyzing a placenta of a pig placenta e.g., such as that disclosed in [31] JP 2002212046, the content of which is incorporated herein by reference.

In some embodiments the compositions/formulations of the invention are substantially devoid/free of a Rhamnolipid e.g., such as that disclosed in [32] WO 2015/030702, the content of which is incorporated herein by reference.

In some embodiments the compositions/formulations of the invention are substantially devoid/free of silicon elastomer e.g., such as that disclosed in [33] U.S. Pat. No. 9,511,034, the content of which is incorporated herein by reference.

In some embodiments the compositions/formulations of the invention are substantially devoid/free of protoberberine e.g., such as that disclosed in [34] U.S. Pat. No. 8,846,019, the content of which is incorporated herein by reference.

In some embodiments the compositions/formulations of the invention are substantially devoid/free of one or more of L-ascorbic acid, L-ascorbic acid derivative and a salt thereof e.g., such as that disclosed in [35] EP 3,398,585, the content of which is incorporated herein by reference.

In some embodiments the compositions/formulations of the invention are substantially devoid/free of one or more of cartilage extract, grape seed extract and tomato extract e.g., such as those disclosed in [36] U.S. Pat. No. 7,435,432, the content of which is incorporated herein by reference.

In some embodiments the compositions/formulations of the invention are substantially devoid/free of benfotiamine and/or pyridoxamine e.g., such as those disclosed in [37] U.S. Pat. No. 7,666,442, the content of which is incorporated herein by reference.

In some embodiments the compositions/formulations of the invention are substantially devoid/free of at least one mineral oil such as those disclosed in [38] US 2011/0044920, the content of which is incorporated herein by reference.

In some embodiments the compositions of the invention are substantially devoid/free of one or more of: petrolatum; petrolatum matrix; non-natural or synthetic nitrone derivatives (e.g., as disclosed herein above); a ferment extract from a strain of *Eupenicillium crustaceum* species; biologically active substances of animal origin; a lipid soluble compound; anti-OX40L antibody; IL-1 antagonist e.g., IL-1 receptor and IL-1RAcP; thick licorice extract; hydrogen peroxide; a fruit extract from pomegranate; phenoxy-ethanol; one or more of ferulic acid, caffeic acid, tannic acid and ellagic acid; essential oil blend (e.g., as disclosed herein above); silicon polymers; ximenynic acid; an extract of Momordica grosvenori fruit; cellulose ether; of a water-soluble component obtained by hydrolyzing a placenta of a pig placenta; a Rhamnolipid; silicon elastomer; protoberberine; one or more of L-ascorbic acid, L-ascorbic acid derivative and a salt thereof; one or more of cartilage extract, grape seed extract and tomato extract; benfotiamine and/or pyridoxamine; at least one mineral oil; or any combination thereof, optionally in combination with one or more of the aforementioned anti-glycation agents disclosed in [27] US 2008/0044373.

In some embodiments the compositions of the invention are substantially devoid/free of one or more of: *Silybum*

(Milk thistle) oil, ultra fine Dead Sea minerals and/or salts, at least one mineral oil and Myrrh oil.

In some embodiments the compositions of the invention are substantially devoid/free of one or more of: *Silybum* (Milk thistle) oil, ultra fine Dead Sea minerals and/or salts and Myrrh oil.

As used herein the terms "substantially devoid" or "substantially free" may be envisaged as containing traces amounts of the ingredient the terms refer to, when applicable, at amounts that illustrate no activity e.g., no anti-glycation and/or AGEs formation inhibition activity. At times the traces amounts are below 0.1%, 0.09%, 0.08%, 0.07%, 0.06%, 0.05%, 0.04%, 0.03%, 0.02% or 0.01% (w/w).

Unless otherwise noted, the percentages of the various ingredients of the compositions of the present disclosure are provided herein in weight per weight ratio (w/w).

The term "topical" as used herein refers to the application of a composition/formulation according to the invention directly onto at least a portion of a subject's skin (human's or non-human's skin) so as to achieve a desired effect, e.g., cosmetic or therapeutic effect, at the site of application. In some embodiments, the desired effect is achieved at the site of application without inducing one or more systemic effects. In other embodiments, the composition/formulation of the invention induces at least a partial systemic effect which contributes to the induction of at least one desired effect.

The term "skin" as used herein refers to any part of the human or animal skin, including the whole surface thereof, hair and nails. At times, hair is excluded.

In some embodiments the skin is a skin of a subject susceptible to or having an accumulation of AGE.

The term "treatment" as used herein refers to the administration (e.g., topical administration) of an effective amount of a composition/formulation of the present invention effective to illustrate the desired effect. For example, to ameliorate undesired symptoms associated with a skin disease, to prevent the manifestation of such symptoms before they occur, to slow down the progression of the disease/condition, slow down the deterioration of symptoms, to enhance the onset of remission period, slow down the irreversible damage caused in the progressive chronic stage of the disease/condition, to delay the onset of said progressive stage, to lessen the severity or cure the disease/condition, to improve survival rate or more rapid recovery, or to prevent the disease/condition form occurring or a combination of two or more of the above.

The administration of the compositions/formulations of the invention may be according to a dosage and administration regimen defined by routine testing.

The "effective amount", whether a therapeutically or cosmetically effective amount for purposes herein, is determined by such considerations as may be known in the art. The amount must be effective to achieve one or more of the above desired therapeutic or cosmetic effects, depending, inter alia, on the type and severity of the disease/condition to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile, a variety of pharmacological parameters such as half life on the skin, on undesired side effects, if any, on factors such as the individual subject, the age and the gender thereof, etc. In a particular embodiment the term is envisages as an amount effective in preventing and/or reducing and/or inhibiting glycation and/or AGE formation and/or the accompanied beneficial effect of this action. As pointed out above, the exact amount required will vary from case to case. An appropriate effective amount may be determined by one of ordinary skill in the art using routine experimentation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is noted that the embodiments provided herein above and below in connection with a specific aspect of the invention may be applicable mutatis-mutandis to the other disclosed aspects of the invention. For example, embodiments disclosed herein in connection with the compositions of the invention and/or the constitutes thereof are applicable mutatis-mutandis to formulations of the invention, to combinations of the invention, to anti-glycation compositions of the invention, to uses of same, to methods utilizing same etc.

As used herein above and below the term "about" refers to ±10% of the indicated value, at times to ±5% of the indicated value.

As used herein, the singular form "a", "an" and "the" include plural references unless the context clearly dictates otherwise. For example, the term "an extract" or "at least one extract" may independently include a plurality of extracts, including a variety thereof.

Various embodiments and aspects of the present invention as delineated hereinabove and as claimed in the claims section below find experimental support in the following examples.

DETAILED DESCRIPTION OF EMBODIMENTS

The following examples are not in any way intended to limit the scope of the invention as claimed.

Example 1: Dead Sea Extract

A commercial preparation of a Dead Sea extract referred to herein as "Osmoter" or "Osmoter™" or "Mineral Skin Osmoter" was used. The preparation is also known as "Maris Sal" or "Maris Aqua" (Dead Sea Water, DSW).

Product name: Dead Sea Works LTD. The product comprises the following ions: $Mg^{+2}$ (92,500 mg/L), $Ca^{+2}$ (38,000 mg/L), $K^{+}$(1,400 mg/L), $Na^{+}$(2,000 mg/L), $Sr^{+2}$ (800 mg/L), $Cl^{-}$(345,000 mg/L) and $Br^{-}$(11,500 mg/L).

Various concentrations of the "Osmoter" preparation were tested e.g., as detailed herein below, for example 0.2%, 0.5% and 2.0% (w/w).

Example 2: Plants Extracts

The following plants extracts were used:
A. *Commiphora myrrha* Extract
Product name: Glycerolat® of Myrrh, Produced & Commercialized by CEP-SOLABIA Group.

*Commiphora myrrha* resin extract contain: 50% Glycerin; 49.25% water; 0.65% *Commiphora abyssinica* resin extract; and 0.10% Potassium sorbate.

B. *Silybum marianum* (Milk Thistle) Extract

Product name: ACTIPHYTE™ MILK THISTLE GL80NP, Produced & Commercialized by LIPOTEC USA, INC.

*Silybum marianum* seeds extract contain: 64% Glycerin; *Silybum marianum* Extract 20%; and water 16%.

C. Jujube extract

Product name: Jujube extract BG-J Maruzen Pharmaceutical Co., Ltd.

Jujube extract contain: 5% *Ziziphus jujube* extract; 47.5% Butylene glycol; and 47.5% water.

Various concentrations of the extracts were tested e.g., as detailed herein below, for example 0.5%, 1%, 5.0% and 10% (w/w).

It is noted that further plants extracts were tested and found incompatible either in view of being too dark and incompatible with the measurements detailed herein below or in view of being too viscous and difficult to handle, and/or illustrated no AGEs inhibition effect.

Example 3: Preparation of Various Compositions and Complexes

The compositions of the present disclosure were prepared by diluting the individual extracts. Combinations of various extracts were prepared by mixing the extracts constituting thereof in appropriate concentrations to reach the final concentration as noted. The order of the addition of the extracts was of no importance.

It is noted that the percentages of the aforementioned extracts in the compositions of the present disclosure are provided herein above and below in weight per weight ratio (w/w) i.e., the weight in grams of the extract per 100 gram total weight of the composition.

Various compositions were tested as detailed herein below. Inter-alia, the specific complexes detailed in Table 1 were tested:

TABLE 1 tested complexes

| Complex Name | Jujube extract | Myrrh extract | Osmoter | Silybum extract |
|---|---|---|---|---|
| Complex 1 | 0.5% | 0.5% | 0.2% | — |
| Complex 2 referred to herein also as Triple-A complex or Trianti-A.G.E complex | — | 0.5% | 0.2% | 1.0% |
| Complex 3 | 0.5% | 0.5% | 0.2% | 1.0% |

Example 4: AGEs Accumulation Models

AGEs accumulation measurement in the laboratory is challenging as their accumulation takes a lot of time in terms of months and years. Several laboratory methods known in the art have been developed to evaluate AGEs accumulation by acceleration in vitro models for at least 3 weeks.

In the present study the ability of various compositions and complexes of the present disclosure to inhibit glycation of biomolecules and to inhibit the formation of AGEs which are glycation products of these biomolecules was carried out utilizing two in-vitro complementary assays for AGEs accumulation (See [39] and [40]).

In one assay, bovine serum albumin (BSA)-Glucose AGEs accumulation model was used and in the other assay Collagen-Glucose accumulation model was used.

In the two assays, the proteins were incubated with a solution of the reducing sugar D-glucose.

The AGEs formation detection was caned out by measuring the fluorescence (excitation wavelength 350 nm; emission wavelength 450 nm).

Before incubation, the samples were measured for T0 (time zero) at excitation/emission 350/450 nm. T0 was calculated as follows:

RFU T0=[RFU(Protein+glucose+extract)−RFU(glucose+extract)]

The samples were placed in glass vials, protected from light, and incubate at 37° C. for 7, 8, 14 or 23 days.

After incubation, 200 μl of each sample were placed in a UV 96 wells dish and measured at excitation/emission 350/450 nm. The results were calculated as follows:

$RFU_{after\ incubation}$=[RFU (protein+glucose+extract)−RFU $(_{glucose}$+extract)]

Final results were calculated as $RFU_{final}$= $[RFU_{after\ incubation}-RFU_{T0}]$ The complexes detailed in Table 1 were tested.

Further samples were as follows:
1. DDW (double distilled water)—as untreated control.
2. Triple-A Complex (Complex 2 in Table 1, also referred to herein as
Trianti-A.G.E complex) (Osmoter 0.2%, Myrrh resin extract 0.5%, *Silybum* extract 1%).
3. Myrrh resin extra (*Commiphora abyssinica*): 5%, 1% and 0.5%.
4. Osmoter: 2%, 0.5% and 0.2%.
5. *Silybum* extract (*Silybum marianum* seed extract): 1%.

Further details regarding each assay are provided below:

A. BSA Assay

The final sample volume was 3 ml in a glass vail contained a final concentration of 6 mg/ml BSA, 0.2 M D-glucose, and 50 mM PBS (phosphate buffer). The addition of the extracts/Osmoter was in % of (w/w).

Samples were done in 4 replicates. The untreated control was a 6 mg/ml BSA in 50 mM PBS solution with no D-glucose.

A blank sample (BSA no glucose) was prepared for each sample by mixing 6 mg/ml BSA, 0.2 M glucose, and extract/Osmoter.

B. Collagen Assay

The final sample volume was 3 ml in a glass vail contained a final concentration of 1 mg/ml Collagen, 0.02 M D-glucose, and 50 mM PBS. The addition of the extracts/Osmoter was in % of (w/w).

Samples were done in 4 replicates. The untreated control was a 1 mg/ml Collagen in 50 mM PBS solution with no D-glucose.

A blank sample (Collagen no glucose) was prepared for each sample by mixing 1 mg/ml Collagen, 0.02M glucose, and extract/Osmoter.

The results of the study are presented in FIG. 1 to FIG. 6.

FIG. 1 illustrates the results obtained in the BSA assay tested with Complex 1, Complex 2 (Triple-A complex, also referred to herein as Trianti-A.G.E complex), Complex 3 and each of the individual extracts i.e., Jujube extract (0.5%), Myrrh extract (0.5%), Osmoter (0.2%) and *Silybum* extract (1.0%). The figure depicts the auto-fluorescence (AF) of AGEs generation by BSA and Glucose after 14 days incubation at 37° C. The figure illustrates that out of the four individual extracts, the Osmoter inhibited the AGEs formation to the most extent. The figure further illustrates that out of the three tested complexes, Complex 2 (Triple A-complex) inhibited the AGEs formation to the most extent. As per Complex 3, having all of the four extracts, the inhibition effect illustrated with the individual extracts was diminished. Complex 3 actually demonstrated an increase in AGEs formation.

Figure 2:
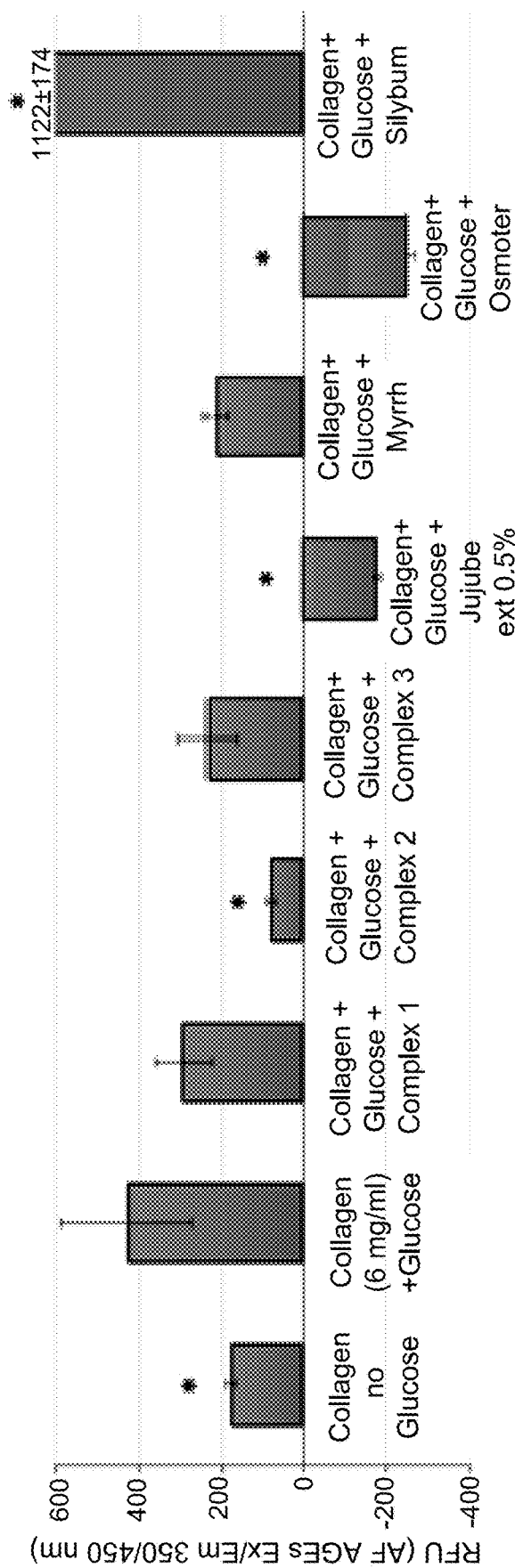
FIG. 2 illustrates auto-fluorescence results of AGEs generation utilizing a Collagen assay as observed for various complexes, compositions, and extracts.

FIG. 2 illustrates the results obtained in the Collagen assay tested with Complex 1, Complex 2 (Triple-A complex, also referred to herein as Trianti-A.G.E complex), Complex 3 and each of the individual extracts i.e., Jujube extract (0.5%), Myrrh extract (0.5%), Osmoter (0.2%) and *Silybum* extract (1.0%). The figure depicts the auto-fluorescence (AF) of AGEs generation by Collagen and Glucose after 14 days incubation at 37° C. The figure illustrates that out of the four individual extracts, the Osmoter inhibited the AGEs formation to the most extent and that the *Silybum* extract actually demonstrated an increase in AGEs formation The figure further illustrates that out of the three tested complexes, Complex 2 (Triple A-complex) inhibited the AGEs formation to the most extent.

Figure 3:
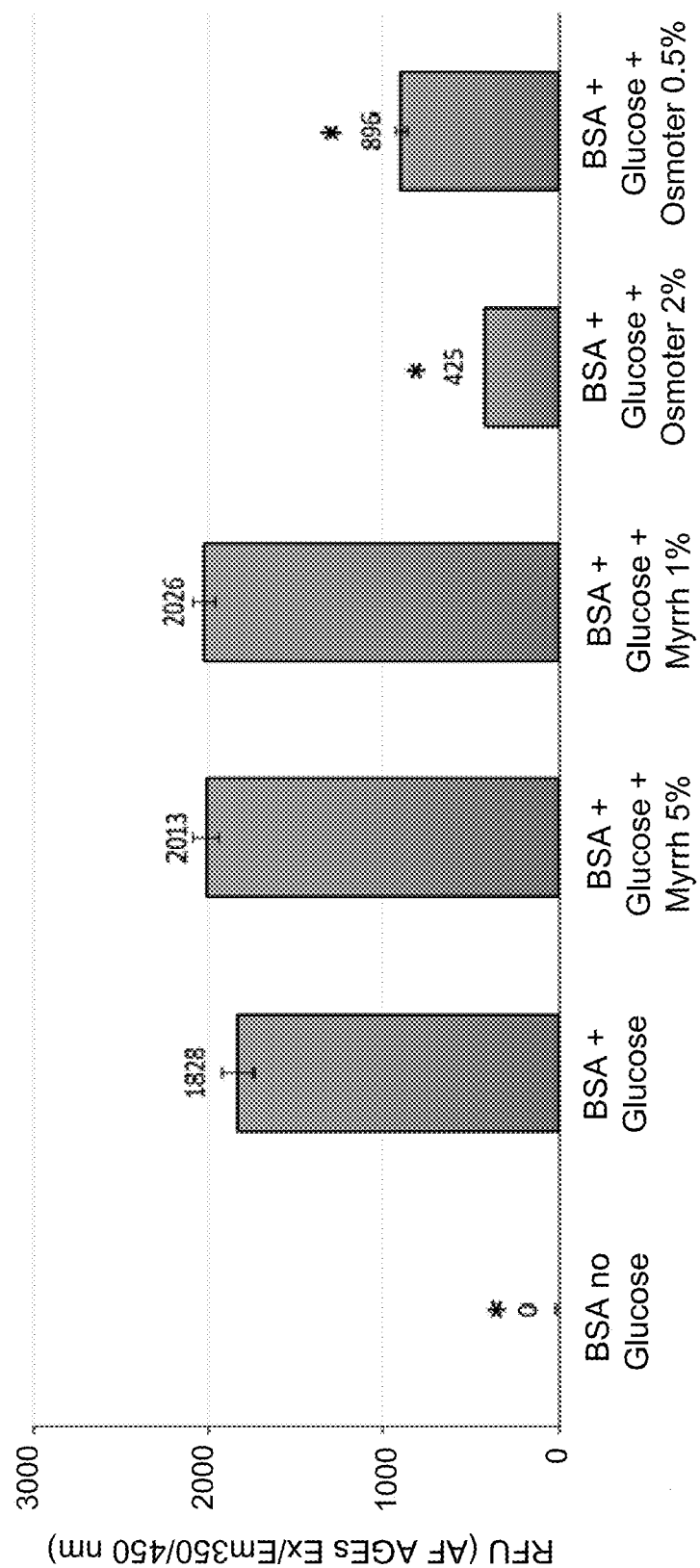
FIG. 3 illustrates auto-fluorescence results of AGEs generation utilizing a BSA assay as observed with Myrrh resin extract and the Dead Sea extract "Osmoter".
Figure 4:
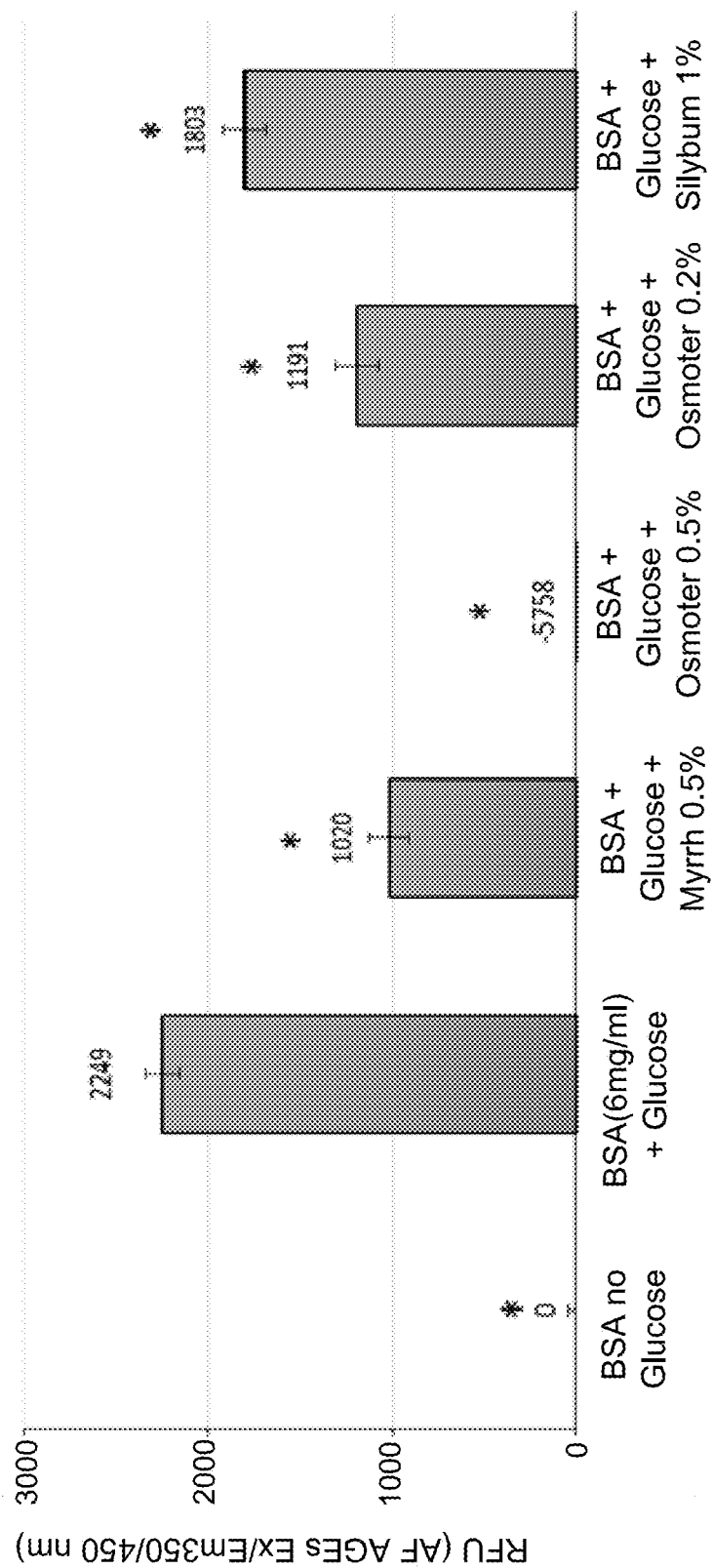
FIG. 4 illustrates auto-fluorescence results of AGEs generation utilizing a BSA assay as observed with Myrrh resin extract, the Dead Sea extract "Osmoter" and *Silybum* seeds extract.

FIG. 3 depicts the auto-fluorescence (AF) of AGEs generation on BSA after exposure to Myrrh resin extract and Osmoter. Each sample contained 6 mg/ml BSA, 0.2 M D-glucose and 5%/1% Myrrh resin extract (w/w) or 2%/0.5% Osmoter (w/w). Negative Control was used as 6 mg/ml BSA without D-glucose. Samples were incubated at 37° C. for 14 days. AF was measure as Em/Ex 350/450 nm. *Pvalue<0.001 vs (BSA+glucose) sample. The figure illustrates that in the BSA model, after 14 days incubation the Myrrh extract at the specific tested concentrations showed no effect on the AGEs formation. The Osmoter showed good effect that increased with increased concentrations of the Osmoter. The effect is most significant as indicated by the P-value FIG. 4 depicts the auto-fluorescence (AF) of AGEs generation on BSA after exposure to Myrrh resin extract, Osmoter and *Silybum* seeds extract. Each sample contained 6 mg/ml BSA, 0.2M D-glucose and 0.5% Myrrh resin extract (w/w) or 0.5%/0.2% Osmoter (w/w) or 1% *Silybum* seeds extract. Negative control was used as 6 mg/ml BSA without D-glucose. Samples were incubated at 37° C. for 23 days. AF was measure as Em/Ex 350/450 nm. *Pvalue<0.001 vs (BSA+glucose) sample. The figure illustrates that in the BSA model, after 23 days incubation the *Silybum* extract showed the least effect, the Osmoter 0.5% showed the best effect and Myrrh showed an intermediate effect.

Figure 5:
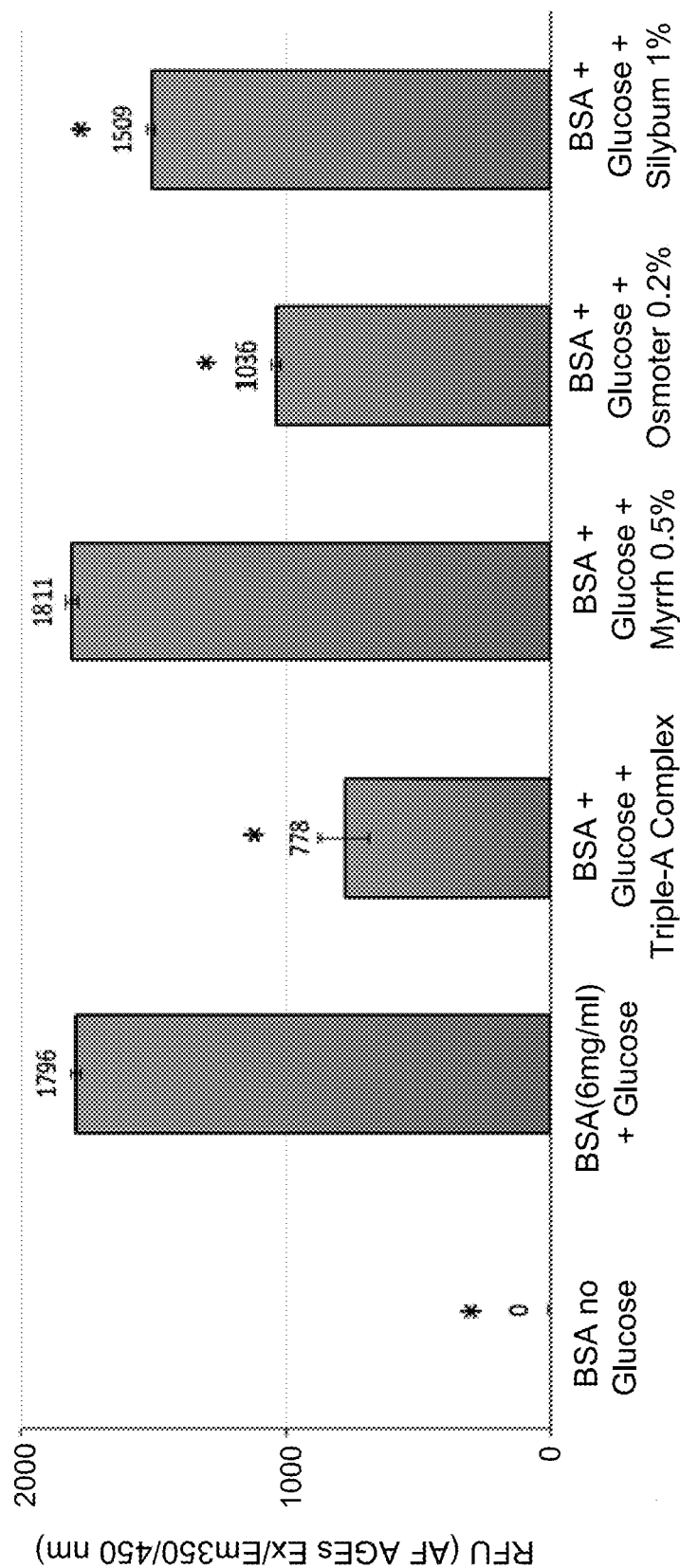
FIG. 5 illustrates auto-fluorescence results of AGEs generation utilizing a BSA assay as observed with Myrrh resin extract, the Dead Sea extract "Osmoter", *Silybum* seeds extract and a complex comprising the three extracts.

FIG. 5: depicts the auto-fluorescence (AF) of AGEs generation on BSA after exposure to Myrrh resin extract, Osmoter, *Silybum* seeds extract and Triple-A complex (also referred to herein as Trianti-A.G.E complex). Each sample contained 6 mg/ml BSA, 0.2 M D-glucose and Triple-A Complex or 0.5% Myrrh resin extract (w/w) or 0.2% Osmoter (w/w) or 1% *Silybum* seeds extract. Negative control was used as 6 mg/ml BSA without D-glucose. Samples were incubated at 37° C. for 14 days. AF was measure as Em/Ex 350/450 nm. *Pvalue<0.001 vs (BSA+glucose) sample. The figure illustrates that in the BSA model the Osmoter showed the best effect out of the three extracts and the Triple-A complex showed the best effect.

Figure 6:
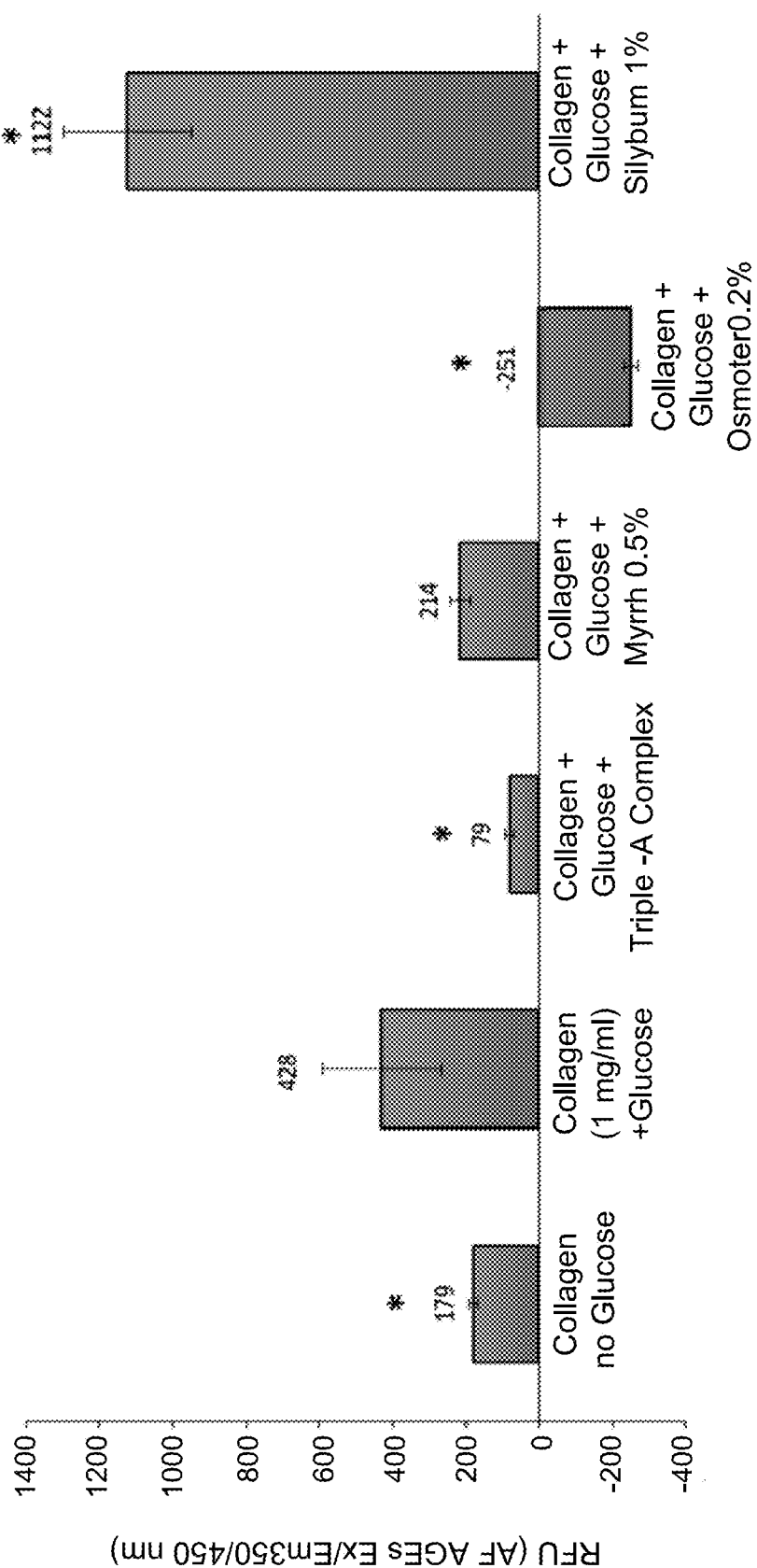
FIG. 6 illustrates auto-fluorescence results of AGEs generation utilizing a Collagen assay as observed with Myrrh resin extract, the Dead Sea extract "Osmoter", *Silybum* seeds extract and a complex comprising the three extracts.

FIG. 6: depicts the auto-fluorescence (AF) of AGEs generation on Collagen after exposure to Myrrh resin extract, Osmoter, *Silybum* seeds extract and Triple-A complex (also referred to herein as Trianti-A.G.E complex). Each sample contained 1 mg/ml Collagen, 0.02M D-glucose and Triple-A Complex or 0.5% Myrrh resin extract (w/w) or 0.2% Osmoter (w/w) or 1% *Silybum* seeds extract. Negative control was used as 1 mg/ml Collagen without D-glucose. Samples were incubated at 37° C. for 14 days. AF was measure as Em/Ex 350/450 nm. *P-value<0.05 vs (Collagen+glucose) sample. The figure illustrates that in the Collagen model, which is a model utilizing a skin protein, after 14 days incubation the *Silybum* extract showed no inhibition effect. The Osmoter, Myrrh and the Triple-A complex showed an inhibition effect with the Osmoter and Triple-A complex being most significant as indicated by the P-values. The figure further illustrates that although the individual *Silybum* extract did not illustrate AGEs inhibition effect (even on the contrary as this extract illustrated RFU of 1122 compared to RFU of 428 of collagen and glucose only), the combination thereof with the Osmoter and the Myrrh extract illustrated a significant inhibition effect of 79 RFU which is much more efficient then the sum effect exhibited by the individual extracts i.e., 214 RFU of the Myrrh extract, –251 RFU of the Osmoter and 1122 RFU of the *Silybum* extract).

Example 5: Oxygen Radical Absorbance Capacity (ORAC)—Anti Oxidation Test

The anti-oxidation ability of various compositions and complexes of the present disclosure was tested utilizing ORAC assay. The ORAC assay was performed as described by Huang et al., [41].

Briefly, the ORAC assay measures the oxidative degradation of the fluorescent molecule (either beta-phicoerythrin or fluorescein) after being mixed with free radical generators such as azo-initiator compounds. Azo-initiators are considered to produce peroxyl free radical by heating, which damages the fluorescent molecule, resulting in the loss of fluorescence. Antioxidant is able to protect the fluorescent molecule from the oxidative degeneration. The degree of protection is quantified using a fluorometer.

The fluorescent intensity decreases as the oxidative degeneration proceeds, and this intensity is recorded for 90 minutes after the addition of the azo-initiator (free radical generator). The degeneration (or decomposition) of fluorescein that is measured as the fluorescence delay becomes less prominent by the presence of antioxidants. Decay curves (fluorescence intensity vs. time) are recorded and the area between two decay curves (with or without antioxidant) is calculated. Subsequently, the degree of antioxidant-mediated protection is quantified using the antioxidant trolox (a vitamin E analogue) as a standard. Different concentrations of Trolox are used to make a standard curve, and test samples are compared to this.

ORAC measures Oxygen Radical Absorbance Capacity expressed as micromole Trolox equivalent (TE) per microliter of the sample (μM TE/μl sample). To each test well, a 150 μl of 1.1 mM sodium fluorescein solution was added. In addition, blank wells received 40 μl of PBS buffer (pH 7.4), while standards received 40 μl of Trolox® at a concentration range of 500-7.8 μM. Trolox standards were prepared for a calibration curve. Samples were prepared at concentrations of x1 and x10 of the Triple-A complex (also referred to herein as Trianti-A.G.E complex) and the individual extracts constituting thereof, diluted with DDW.

10 μl of the tested samples were added to each well and 30 μl of PBS buffer were added for a final volume of 40 μl.

Fresh preparation of 2,2'-Azobis(2-amidinopropane) dihydrochloride (AAPH) dissolved in PBS buffer (pH 7.4) to a final concentration of 0.11 M mM and made fresh daily was used. This solution was added immediately before measuring the plate in the plate reader.

The plate was then allowed to equilibrate by incubating for a minimum of 30 minutes in the Synergy HT Multi-Detection Microplate Reader at 37° C. After adding AAPH solution, the reaction was started immediately, and kinetics was read at 2 min for 90 min (a total of 45 points) at 37° C. at Em/Ex of 485/520 nm.

Calculations–based calculation of S=Area Under Curve of Trolox=(0.5+f1/f0+f2/f0+f3/f0+ . . . f44/f0+f45/f0)×2. Where f0 is the value of time 0, f1 is the value after 2 min and so on. Calculation the area was done by sum all ratio of fx/f0.

$ORAC_{FL}$ fluorescence was read every 2 min for 90 min. Peroxyl radical-induced oxidation started immediately after AAPH addition. Results were quantified by comparison with Trolox calibration curves. Total antioxidant capacity was calculated by measuring the area below the kinetic curve.

Base on the linear calibration curve the samples were calculated and dilution factor was added (×10).

The tested samples are detailed in Table 2

TABLE 2 tested samples

| # | Sample name | % at × 1 concentration | % at × 10 concentration |
|---|---|---|---|
| 1 | Untreated (DDW) | — | — |
| 2 | Triple-A Complex (also referred to herein as Trianti-A.G.E complex) | Osmoter - 0.2% Myrrh - 0.5% Silybum - 1.0% | Osmoter - 2.0% Myrrh - 5.0% Silybum - 10.0% |
| 3 | Myrrh Extract | 0.5% | 5.0% |
| 4 | Osmoter (OSM) | 0.2% | 2.0% |
| 5 | Silybum Extract | 1.0% | 10.0% |
| 6 | Osmoter + Myrrh Extract | Osmoter - 0.2% Myrrh - 0.5% | Osmoter - 2.0% Myrrh - 5.0% |
| 7 | Osmoter + Silybum Extract | Osmoter - 0.2% Silybum - 1.0% | Osmoter - 2.0% Silybum - 10.0% |
| 8 | Myrrh Extract + Silybum Extract | Myrrh - 0.5% Silybum - 1.0% | Myrrh - 5.0% Silybum - 10.0% |

Figure 7:
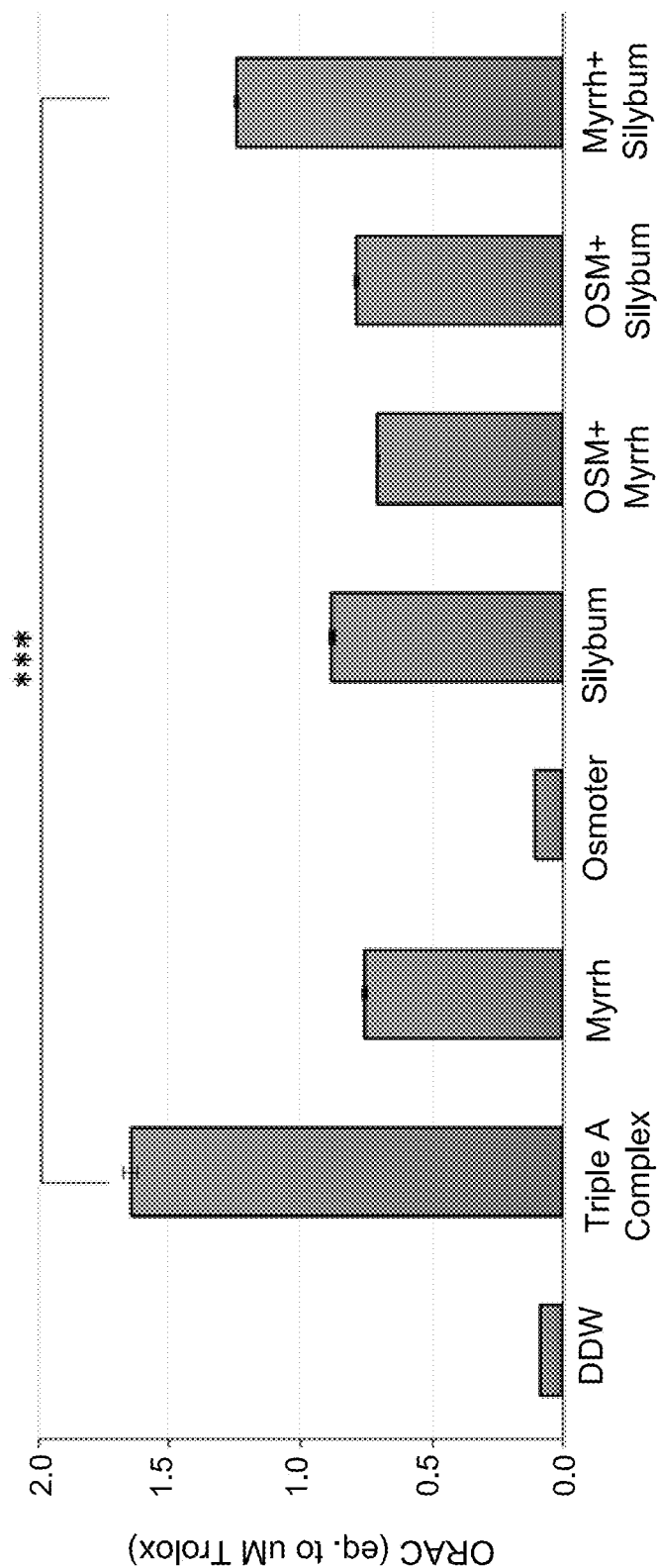
FIG. 7 illustrates the Oxygen Radical Absorbance Capacity (ORAC) results as observed with Myrrh resin extract, the Dead Sea extract "Osmoter", *Silybum* seeds extract, combinations of two of each of said extracts and a complex comprising the three extracts.
Figure 8:
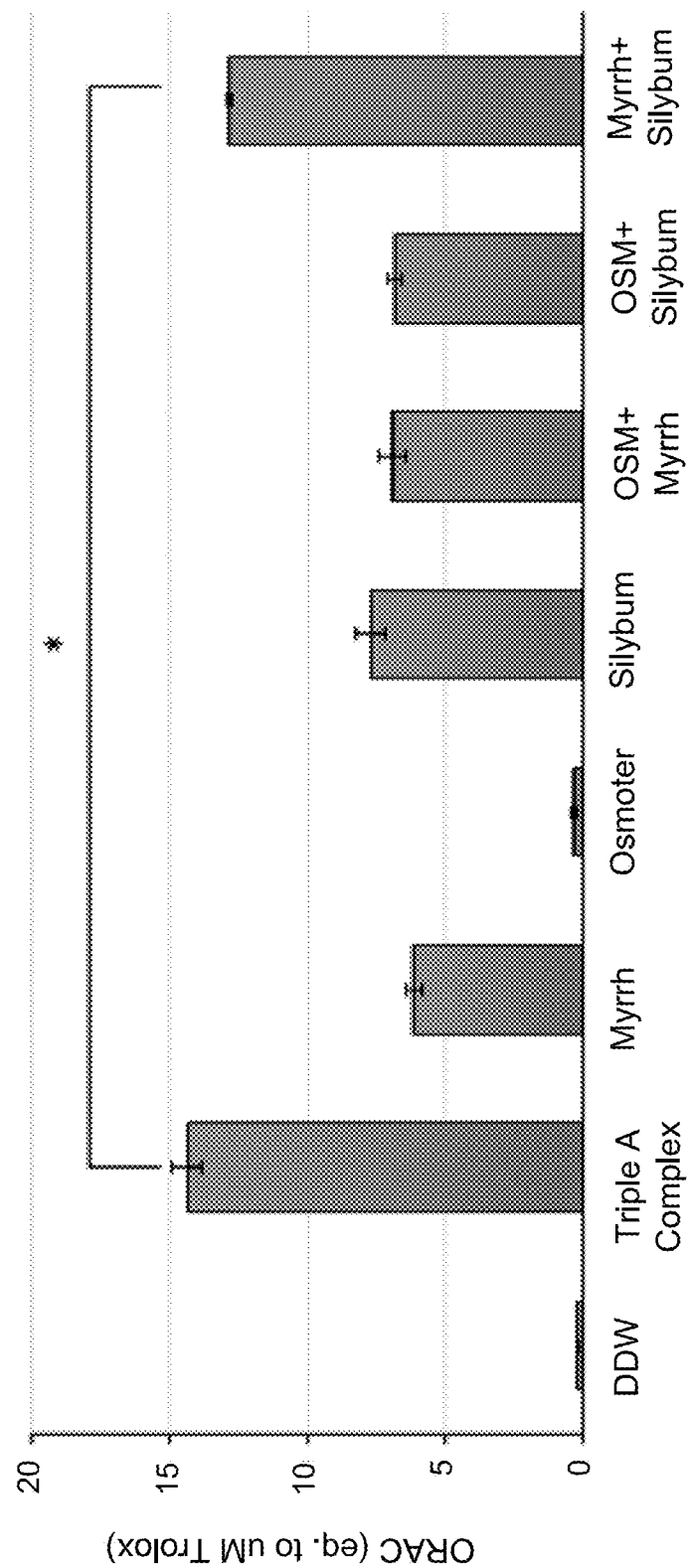
FIG. 8 illustrates the Oxygen Radical Absorbance Capacity (ORAC) results as observed with Myrrh resin extract, the Dead Sea extract "Osmoter", *Silybum* seeds extract, combinations of two of each of said extracts and a complex comprising the three extracts.

FIG. 7 illustrates the results obtained in the ORAC assay of the samples listed in Table 2 at x1 concentration. ***P-value<0.0001. FIG. 8 illustrates the results obtained in the ORAC assay of the samples listed in Table 2 at ×10 concentration. *P-value<0.05. The ORAC was measure as Em/Ex 485/520 nm and the results are presented as an equivalent to µM Trolox/µl sample vs Triple-A complex.

Both FIG. 7 and FIG. 8 illustrate the improved anti-oxidant capability of the Triple-A complex (also referred to herein as Trianti-A.G.E complex) compared to each of the individual extracts as well as compared to di-components combinations of the extracts.

Among the individual extracts, the Osmoter illustrated the least anti-oxidation properties. Myrrh extract and Silybum extract each illustrated anti-oxidation properties, alone and in combination.

Without wishing to be bound by theory, the presence of Myrrh extract in the composition of the present invention advantageously provides the composition both inhibition of AGEs formation characteristic and antioxidation characteristic, the latter may be beneficial both to the skin as well as for the stability of the composition, protecting same from effects associated with exposure to oxygen. The antioxidation properties illustrated with the Silybum extract are also beneficial.

FIG. 7 illustrates that combining the Osmoter with each of Myrrh and Silybum extracts reduced the anti-oxidation effect compared to that of the single extract. Surprisingly, while the combination of Myrrh and Silybum extracts illustrated an antioxidation effect that is smaller than the sum of the effect illustrated with the individual extracts, the Triple-A complex, with the Osmoter and these two extracts, illustrated an effect that is better than the sum of the Osmoter and the combination of Myrrh and Silybum, indicating an advantage of the studied Triple-A complex. Similar results are illustrated in FIG. 8.

Example 6: A Study on Human Skin Organ Culture

Skin Explants Preparation

Human living skin explants are prepared from an abdominoplasty (aesthetic surgery) e.g., from a 20-60-year-old Caucasian woman after obtaining informed consent by the hospital e.g., Soroka Hospital, Beer Sheva #0258-19-SOR. Adipose tissue are removed and explants of 0.16 $cm^2$ are prepared using a press knife. The explants are maintained in survival cell culture conditions at 37° C. in a humid atmosphere enriched with 5% $CO_2$ in DMEM (Dulbecco's Modified Eagle's Medium) explant medium contains 100 U/ml penicillin, and 100 U/ml streptomycin (PSA).

Topical Treatment

Topical treatment groups included: For example, Triple-A Complex (also referred to herein as Trianti-A.G.E complex) or 0.5% Myrrh resin extract or 0.2% Osmoter or 1% Silybum seeds extract. Other compositions and complexes are equivalently tested. The products are tested by topical application of 3 µl of each solution on the skin explants epidermis. Treatments are performed on day 0 and every 2 days until sampling on e.g., day 9 (for 4 applications). For fixation, the explants are immersed in buffered formalin at RT for 24 h.

Staining and Immunostainings

After fixation for 24 h in buffered formalin, samples are dehydrated and impregnated in paraffin using dehydration automat. Samples are cut by a microtome and 5-µm-thick sections are made and the sections are mounted on histological glass slides. General morphology (viability control): Masson's trichrome staining, Goldner variant are performed on formol fixed paraffin-embedded skin sections. This staining, alternative to classical Hematoxylin Erythrosine Saffron, allows a fine evaluation of the cellular and tissue morphology. Immunostainings of CML and Pentosidine are carried out using, respectively, an anti-CML monoclonal antibody and an anti-pentosidine monoclonal antibody, with an avidin/biotin amplifier system and revealed by VIP, a substrate of peroxidase. Microscopical observations are realized using a light microscope (magnification ×40). Pictures are digitized with a camera with designated storing software. Immunostainings are assessed by microscopical observation and image analysis.

ORAC on HSOC lysate at different time points is measured e.g., after 30 min incubation, after 1 hr incubation, after 24 hr incubation and after 48 hr incubation with the tested samples e.g., Triple-A complex and components (concentration ×1 in DDW, as in the complex, and concentration ×10 in DDW). Other concentrated complexes are tested e.g., 11.8% Myrrh extract, 29.4% Silybum extract and 58.8% Osmoter.

The Triple-A complex (also referred to herein as Trianti-A.G.E complex) is expected to show anti-oxidation characteristics better that those of the individual extracts. At times, the anti-oxidation effect of the Triple-A complex is a synergistic effect.

ILLUSTRATIVE EMBODIMENTS

The following embodiments are illustrative and not intended to limit the claimed subject matter.

EMBODIMENT 1 A composition comprising as an active combination at least one Dead Sea extract and at least one Myrrh tree extract.

EMBODIMENT 2 The composition according to EMBODIMENT 1, wherein said composition further comprise at least one Silybum extract and/or at least one Jujube extract.

EMBODIMENT 3 The composition according to EMBODIMENT 1 or 2, wherein said at least one Dead Sea extract is a mixture of natural materials obtained from the waters of the Dead Sea and/or the mud surrounding the Dead Sea and/or the soil bed of the Dead Sea.

EMBODIMENT 4 The composition according to any one of EMBODIMENTS 1 to 3, wherein said at least one Dead Sea extract is Dead Sea water.

EMBODIMENT 5 The composition according to any one of EMBODIMENTS 1 to 4, wherein said at least one Dead Sea extract is Dead Sea water and wherein a ratio between the magnesium and calcium divalent cations to the potassium and sodium monovalent cations in the Dead Sea water is between about 20 to about 55.

EMBODIMENT 6 The composition according to any one of EMBODIMENTS 1 to 5, wherein said at least one Dead Sea extract is Dead Sea mud.

EMBODIMENT 7 The composition according to any one of EMBODIMENTS 1 to 6, wherein said at least one Dead Sea extract constitutes between about 0.01% to about 2.40% (w/w) of the total weight of the composition.

EMBODIMENT 8 The composition according to any one of EMBODIMENTS 1 to 7, wherein said at least one Myrrh tree extract is *Commiphora myrrha* tree extract.

EMBODIMENT 9 The composition according to any one of EMBODIMENTS 1 to 8, wherein said at least one Myrrh tree extract is *Commiphora myrrha* resin tree extract.

EMBODIMENT 10 The composition according to any one of EMBODIMENTS 1 to 9, wherein said at least one Myrrh tree extract constitutes between about 0.01% to about 1.50% (w/w) of the total weight of the composition.

EMBODIMENT 11 The composition according to EMBODIMENT 10, wherein said at least one Myrrh tree extract constitutes 0.50% (w/w) of the total weight of the composition.

EMBODIMENT 12 The composition according to any one of EMBODIMENTS 1 to 11, wherein said composition further comprises at least one *Silybum* extract.

EMBODIMENT 13 The composition according to EMBODIMENT 12, wherein said at least one *Silybum* extract is *Silybum marianum* extract.

EMBODIMENT 14 The composition according to EMBODIMENT 13, wherein said *Silybum marianum* extract is *Silybum marianum* seeds extract.

EMBODIMENT 15 The composition according to any one of EMBODIMENTS 2 to 14, wherein the *Silybum* extract constitutes between about 0.01% to about 1.50% (w/w) of the total weight of the composition.

EMBODIMENT 16 The composition according to EMBODIMENT 15, wherein the *Silybum* extract constitutes about 1.00% (w/w) of the total weight of the composition.

EMBODIMENT 17 The composition according to any one of EMBODIMENTS 1 to 16, wherein said composition comprises at least one Dead Sea extract, at least one Myrrh tree extract and at least one *Silybum* extract, wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the *Silybum* extract constitutes between about 0.01% to about 1.50% (w/w) of the total weight of the composition.

EMBODIMENT 18 The composition according to EMBODIMENT 17, wherein the Dead Sea extract constitutes about 0.20% (w/w) of the total weight of the composition, the Myrrh tree extract constitutes about 0.50% (w/w) of the total weight of the composition, and the *Silybum* extract constitutes about 1.00% (w/w) of the total weight of the composition.

EMBODIMENT 19 The composition according to any one of EMBODIMENTS 1 to 18, wherein said composition is free of Jujube extract.

EMBODIMENT 20 The composition according to any one of EMBODIMENTS 1 to 11, wherein said composition further comprises at least one Jujube extract.

EMBODIMENT 21 The composition according to EMBODIMENT 20, wherein said at least one Jujube extract is *Ziziphus jujube* fruit extract.

EMBODIMENT 22 The composition according to EMBODIMENT 20 or 21, wherein the Jujube extract constitutes between about 0.01% to about 1.50% (w/w) of the total weight of the composition.

EMBODIMENT 23 The composition according to EMBODIMENT 22, wherein the Jujube extract constitutes about 0.50% (w/w) of the total weight of the composition.

EMBODIMENT 24 The composition according to any one of EMBODIMENTS 20 to 23, wherein said composition comprises at least one Dead Sea extract, at least one Myrrh tree extract and at least one Jujube extract, wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the Jujube extract constitutes between about 0.01% to about 1.50% (w/w) of the total weight of the composition.

EMBODIMENT 25 The composition according to EMBODIMENT 24, wherein the Dead Sea extract constitutes about 0.20% (w/w) of the total weight of the composition, the Myrrh tree extract constitutes about 0.50% (w/w) of the total weight of the composition, and the Jujube extract constitutes about 0.50% (w/w) of the total weight of the composition.

EMBODIMENT 26 The composition according to any one of EMBODIMENTS 20 to 25, wherein said composition is free of *Silybum* extract.

EMBODIMENT 27 The composition according to any one of EMBODIMENTS 1 to 26, wherein said composition being an anti-glycation composition.

EMBODIMENT 28 An anti-glycation composition comprising as an active combination at least one Dead Sea extract and at least one Myrrh tree extract.

EMBODIMENT 29 The anti-glycation composition according to EMBODIMENT 28, wherein said composition further comprise at least one *Silybum* extract and/or at least one Jujube extract.

EMBODIMENT 30 The anti-glycation composition according to EMBODIMENT 28 or 29, wherein said at least one Dead Sea extract is a mixture of natural materials obtained from the waters of the Dead Sea and/or the mud surrounding the Dead Sea and/or the soil bed of the Dead Sea.

EMBODIMENT 31 The anti-glycation composition according to any one of EMBODIMENTS 28 to 30, wherein said at least one Dead Sea extract is Dead Sea water.

EMBODIMENT 32 The anti-glycation composition according to any one of EMBODIMENTS 28 to 31, wherein said at least one Dead Sea extract is Dead Sea water and wherein a ratio between the magnesium and calcium divalent cations to the potassium and sodium monovalent cations in the Dead Sea water is between about 20 to about 55.

EMBODIMENT 33 The anti-glycation composition according to any one of EMBODIMENT 28 to 32, wherein said at least one Dead Sea extract is Dead Sea mud.

EMBODIMENT 34 The anti-glycation composition according to any one of EMBODIMENTS 28 to 33, wherein said at least one Dead Sea extract constitutes between about 0.01% to about 2.40% (w/w) of the total weight of the composition.

EMBODIMENT 35 The anti-glycation composition according to any one of EMBODIMENTS 28 to 34, wherein said at least one Myrrh tree extract is *Commiphora myrrha* tree extract.

EMBODIMENT 36 The anti-glycation composition according to any one of EMBODIMENTS 28 to 35, wherein said at least one Myrrh tree extract is *Commiphora myrrha* resin tree extract.

EMBODIMENT 37 The anti-glycation composition according to any one of EMBODIMENT 28 to 36, wherein said at least one Myrrh tree extract constitutes between about 0.01% to about 1.50% (w/w) of the total weight of the composition.

EMBODIMENT 38 The anti-glycation composition according to EMBODIMENT 37, wherein said at least one Myrrh tree extract constitutes 0.50% (w/w) of the total weight of the composition.

EMBODIMENT 39 The anti-glycation composition according to any one of EMBODIMENTS 28 to 38, wherein said composition further comprises at least one *Silybum* extract.

EMBODIMENT 40 The anti-glycation composition according to EMBODIMENT 39, wherein said at least one *Silybum* extract is *Silybum marianum* extract.

EMBODIMENT 41 The anti-glycation composition according to EMBODIMENT 40, wherein said *Silybum marianum* extract is *Silybum marianum* seeds extract.

EMBODIMENT 42 The anti-glycation composition according to any one of EMBODIMENTS 29 to 41, wherein the *Silybum* extract constitutes between about 0.01% to about 1.50% (w/w) of the total weight of the composition.

EMBODIMENT 43 The anti-glycation composition according to EMBODIMENT 42, wherein the *Silybum* extract constitutes about 1.00% (w/w) of the total weight of the composition.

EMBODIMENT 44 The anti-glycation composition according to any one of EMBODIMENTS 28 to 43, wherein said composition comprises at least one Dead Sea extract, at least one Myrrh tree extract and at least one *Silybum* extract, wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the *Silybum* extract constitutes between about 0.01% to about 1.50% (w/w) of the total weight of the composition.

EMBODIMENT 45 The anti-glycation composition according to EMBODIMENT 44, wherein the Dead Sea extract constitutes about 0.20% (w/w) of the total weight of the composition, the Myrrh tree extract constitutes about 0.50% (w/w) of the total weight of the composition, and the *Silybum* extract constitutes about 1.00% (w/w) of the total weight of the composition.

EMBODIMENT 46 The anti-glycation composition according to any one of EMBODIMENTS 28 to 45, wherein said composition is free of Jujube extract.

EMBODIMENT 47 The anti-glycation composition according to any one of EMBODIMENTS 28 to 38, wherein said composition further comprises at least one Jujube extract.

EMBODIMENT 48 The anti-glycation composition according to EMBODIMENT 47, wherein said at least one Jujube extract is *Ziziphus jujube* fruit extract.

EMBODIMENT 49 The anti-glycation composition according to EMBODIMENT 47 or 48, wherein the Jujube extract constitutes between about 0.01% to about 1.50% (w/w) of the total weight of the composition.

EMBODIMENT 50 The anti-glycation composition according to EMBODIMENT 49, wherein the Jujube extract constitutes about 0.50% (w/w) of the total weight of the composition.

EMBODIMENT 51 The anti-glycation composition according to any one of EMBODIMENTS 47 to 50, wherein said composition comprises at least one Dead Sea extract, at least one Myrrh tree extract and at least one Jujube extract, wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the Jujube extract constitutes between about 0.01% to about 1.50% (w/w) of the total weight of the composition.

EMBODIMENT 52 The anti-glycation composition according to EMBODIMENT 51, wherein the Dead Sea extract constitutes about 0.20% (w/w) of the total weight of the composition, the Myrrh tree extract constitutes about 0.50% (w/w) of the total weight of the composition, and the Jujube extract constitutes about 0.50% (w/w) of the total weight of the composition.

EMBODIMENT 53 The anti-glycation composition according to any one of EMBODIMENTS 47 to 52, wherein said composition is free of *Silybum* extract.

EMBODIMENT 54 The composition according to any one of EMBODIMENTS 1 to 53, being a topical composition.

EMBODIMENT 55 The composition according to any one of EMBODIMENTS 1 to 54, being an anti-aging composition.

EMBODIMENT 56 The composition according to any one of EMBODIMENTS 1 to 55, being a synergistic composition.

EMBODIMENT 57 The composition according to any one of EMBODIMENTS 1 to 56, for use in preventing and/or reducing and/or inhibiting the glycation of one or more biomolecules; and/or for use in preventing and/or reducing and/or inhibiting the formation of AGEs.

EMBODIMENT 58 The composition for use according to EMBODIMENT 57, wherein said biomolecule is one or more of at least one protein, at least one lipid and at least one nucleic acid.

EMBODIMENT 59 The composition for use according to EMBODIMENT 58, wherein said biomolecule is at least one protein.

EMBODIMENT 60 The composition for use according to EMBODIMENT 59, wherein said at least one protein is a skin protein.

EMBODIMENT 61 The composition for use according to EMBODIMENT 59 or 60, wherein said at least one protein is an extracellular matrix protein.

EMBODIMENT 62 The composition for use according to EMBODIMENT 61, wherein said extracellular matrix protein is one or more of collagen, vimentin and elastin.

EMBODIMENT 63 The composition for use according to any one of EMBODIMENTS 57 to 62, wherein said AGEs is a protein.

EMBODIMENT 64 The composition for use according to EMBODIMENT 63, wherein said AGEs is a skin protein.

EMBODIMENT 65 The composition for use according to EMBODIMENT 64, wherein said protein is a filamentous protein.
EMBODIMENT 66 The composition for use according to EMBODIMENT 65, wherein said filamentous protein is keratin.
EMBODIMENT 67 The composition for use according to any one of EMBODIMENTS 57 to 62, wherein said AGEs is one or more of a carboxymethyl-lysine (CML), a carboxyethyl lysine (CEL), and a fructose-lysine adduct.
EMBODIMENT 68 The composition for use according to any one of EMBODIMENTS 57 to 62, wherein said AGEs is pentosidine.
EMBODIMENT 69 The composition for use according to any one of EMBODIMENTS 57 to 62, wherein said AGEs is at lease one extracellular matrix protein.
EMBODIMENT 70 The composition for use according to EMBODIMENT 69, wherein said extracellular matrix protein is one or more of collagen, vimentin and elastin.
EMBODIMENT 71 The composition for use according to any one of EMBODIMENTS 57 to 70, wherein said composition is for preventing and/or reducing and/or inhibiting the glycation of lysine residues of at least one protein in a subject.
EMBODIMENT 72 The composition for use according to EMBODIMENT 71, wherein said composition is further used for preventing and/or reducing and/or inhibiting the formation of AGEs of at least one protein.
EMBODIMENT 73 A method of preventing and/or reducing and/or inhibiting the glycation of one or more biomolecules, the method comprising topical application of a composition according to any one of EMBODIMENTS 1 to 56 onto at least a region of the skin of a subject.
EMBODIMENT 74 The method according to EMBODIMENT 73, wherein said biomolecule is one or more of at least one protein, at least one lipid and at least one nucleic acid.
EMBODIMENT 75 The method according to EMBODIMENT 74, wherein said biomolecule is at least one protein.
EMBODIMENT 76 The method according to EMBODIMENT 75, wherein said at least one protein is a skin protein.
EMBODIMENT 77 The method according to EMBODIMENT 75 or 76, wherein said at least one protein is an extracellular matrix protein.
EMBODIMENT 78 The method according to EMBODIMENT 77, wherein said extracellular matrix protein is one or more of collagen, vimentin and elastin.
EMBODIMENT 79 The method according to any one of EMBODIMENTS 73 to 78, wherein said method is for preventing and/or reducing and/or inhibiting the glycation of lysine residues of at least one protein in a subject.
EMBODIMENT 80 A method of preventing and/or reducing and/or inhibiting the formation of AGEs, the method comprising topical application of a composition according to any one of EMBODIMENTS 1 to 56 onto at least a region of the skin of a subject.
EMBODIMENT 81 The method according to EMBODIMENT 80, wherein said AGEs is a protein.
EMBODIMENT 82 The method according to EMBODIMENT 81, wherein said AGEs is a skin protein.
EMBODIMENT 83 The method according to EMBODIMENT 82, wherein said protein is a filamentous protein.
EMBODIMENT 84 The method according to EMBODIMENT 83, wherein said filamentous protein is keratin.
EMBODIMENT 85 The method according to any one of EMBODIMENTS 80 to 84, wherein said AGEs is one or more of a carboxymethyl-lysine (CML), a carboxyethyl lysine (CEL), and a fructose-lysine adduct.
EMBODIMENT 86 The method according to EMBODIMENT 80, wherein said AGEs is pentosidine.
EMBODIMENT 87 The method according to EMBODIMENT 80, wherein said AGEs is at lease one extracellular matrix protein.
EMBODIMENT 88 The method according to EMBODIMENT 87, wherein said extracellular matrix protein is one or more of collagen, vimentin and elastin.
EMBODIMENT 89 Use of the composition according to any one of EMBODIMENTS 1 to 56 for the manufacture of a formulation for preventing and/or reducing and/or inhibiting the glycation of one or more biomolecules and/or for preventing and/or reducing and/or inhibiting the formation of AGEs.
EMBODIMENT 90 The use according to EMBODIMENT 89, wherein said biomolecule is one or more of at least one protein, at least one lipid and at least one nucleic acid.
EMBODIMENT 91 The use according to EMBODIMENT 90, wherein said biomolecule is at least one protein.
EMBODIMENT 92 The use according to EMBODIMENT 91, wherein said at least one protein is a skin protein.
EMBODIMENT 93 The use according to EMBODIMENT 91 or 92, wherein said at least one protein is an extracellular matrix protein.
EMBODIMENT 94 The use according to EMBODIMENT 93, wherein said extracellular matrix protein is one or more of collagen, vimentin and elastin.
EMBODIMENT 95 The use according to any one of EMBODIMENTS 89 to 94, wherein said AGEs is a protein.
EMBODIMENT 96 The use according to EMBODIMENT 95, wherein said AGEs is a skin protein.
EMBODIMENT 97 The use according to EMBODIMENT 95 or 96, wherein said protein is a filamentous protein.
EMBODIMENT 98 The use according to EMBODIMENT 97, wherein said filamentous protein is keratin.
EMBODIMENT 99 The use according to any one of EMBODIMENT 89 to 94, wherein said AGEs is one or more of a carboxymethyl-lysine (CML), a carboxyethyl lysine (CEL), and a fructose-lysine adduct.
EMBODIMENT 100 The use according to any one of EMBODIMENT 89 to 94, wherein said AGEs is pentosidine.
EMBODIMENT 101 The use according to any one of EMBODIMENT 89 to 94, wherein said AGEs is at lease one extracellular matrix protein.
EMBODIMENT 102 The use according to EMBODIMENT 101, wherein said extracellular matrix protein is one or more of collagen, vimentin and elastin.
EMBODIMENT 103 The use according to any one of EMBODIMENTS 89 to 94, wherein said composition is for preventing and/or reducing and/or inhibiting the glycation of lysine residues of at least one protein in a subject.
EMBODIMENT 104 The use according to EMBODIMENT 103, wherein said composition is further used for preventing and/or reducing and/or inhibiting the formation of AGEs of at least one protein.
EMBODIMENT 105 The composition according to any one of EMBODIMENTS 1 to 56 for preventing and/or treating at least one disease or disorder of the skin of a subject, said disease or disorder being associate with and/or being induced by glycation of one or more biomolecules and/or by formation of AGEs.
EMBODIMENT 106 Use of the composition according to any one of EMBODIMENTS 1 to 56 for the manufacture of a formulation for preventing and/or treating at least one disease or disorder of the skin of a subject, said disease or disorder being associate with and/or being induced by glycation of one or more biomolecules and/or by formation of AGEs.

EMBODIMENT 107 A method for treating and/or preventing at least one disease or disorder of the skin of a subject, wherein the disease or disorder being associate with and/or being induced by glycation of one or more biomolecules and/or formation of AGEs, the method comprises topical application of the composition according to any one of EMBODIMENTS 1 to 56 onto the skin of the subject in need thereof.

EMBODIMENT 108 A method for protecting and/or improving the state of the skin of a subject, preventing and/or treating imperfections of the skin of a subject in need thereof, the method comprises topical application of the composition according to any one of EMBODIMENTS 1 to 56 onto the skin of the subject in need thereof, wherein the protecting and/or improving the state of the skin of a subject, preventing and/or treating imperfections of the skin of a subject in need thereof being associated with the composition capability of preventing and/or reducing and/or inhibiting the glycation of one or more biomolecules, and/or the composition capability of preventing and/or reducing and/or inhibiting the formation of AGEs.

EMBODIMENT 109 A method of substantially preventing or delaying the onset of, or substantially preventing or retarding the progression of a condition which is associated with the formation of AGEs in a subject in need thereof, the method comprises administering to the subject a composition according to any one of EMBODIMENTS 1-56.

EMBODIMENT 110 A serum, a lotion, an ointment, a gel, a moisturizer, a sunscreen, a cream, a stick, a spray, an aerosol, foam, a paste, a mousse, a liquid make-up, a foundation, or a make-up comprising the composition according to any one of EMBODIMENTS 1 to 56.

EMBODIMENT 111 The composition according to any one of EMBODIMENTS 1 to 56, being in the form of a serum, a lotion, an ointment, a gel, a moisturizer, a sunscreen, a cream, a stick, a spray, an aerosol, foam, a paste, a mousse, a liquid make-up, a foundation, or a make-up.

EMBODIMENT 112 The composition according to EMBODIMENT 111, formulated as a cosmetic, skin-care, dermatological or a pharmaceutical formulation.

The invention claimed is:

1. A composition comprising as an active combination at least one Dead Sea extract and at least one Myrrh tree extract, wherein said composition is a synergistic composition.

2. The composition according to claim 1, wherein said composition further comprises at least one *Silybum* extract and/or at least one Jujube extract.

3. The composition according to claim 1, wherein said at least one Dead Sea extract is a mixture of natural materials obtained from the waters of the Dead Sea and/or the mud surrounding the Dead Sea and/or the soil bed of the Dead Sea.

4. The composition according to claim 1, wherein said at least one Dead Sea extract is Dead Sea water or Dead Sea mud.

5. The composition according to claim 1, wherein said at least one Dead Sea extract is Dead Sea water and wherein a ratio between the magnesium and calcium divalent cations to the potassium and sodium monovalent cations in the Dead Sea water is between about 20 to about 55.

6. The composition according to claim 1, wherein said at least one Myrrh tree extract is *Commiphora Myrrha* tree extract.

7. The composition according to claim 1, wherein said at least one Myrrh tree extract is *Commiphora Myrrha* resin tree extract.

8. The composition according to claim 1, wherein said composition further comprises at least one *Silybum* extract.

9. The composition according to claim 8, wherein said at least one *Silybum* extract is *Silybum marianum* extract.

10. The composition according to claim 9, wherein said *Silybum marianum* extract is *Silybum marianum* seeds extract.

11. The composition according to claim 1, wherein said composition comprises at least one Dead Sea extract, at least one Myrrh tree extract and at least one *Silybum* extract, wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the *Silybum* extract constitutes between about 0.01% to about 1.50% (w/w) of the total weight of the composition.

12. The composition according to claim 11, wherein the Dead Sea extract constitutes about 0.20% (w/w) of the total weight of the composition, the Myrrh tree extract constitutes about 0.50% (w/w) of the total weight of the composition, and the *Silybum* extract constitutes about 1.00% (w/w) of the total weight of the composition.

13. The composition according to claim 8, wherein said composition is free of Jujube extract.

14. The composition according to claim 1, wherein said composition further comprises at least one Jujube extract.

15. The composition according to claim 14, wherein said at least one Jujube extract is *Ziziphus* Jujube fruit extract.

16. The composition according to claim 14, wherein said composition comprises at least one Dead Sea extract, at least one Myrrh tree extract and at least one Jujube extract, wherein the Dead Sea extract constitutes between about 0.01% to about 2.40% (w/w) of the total weight of the composition, the Myrrh tree extract constitutes between about 0.01% to about 1.50% (w/w) of the total weight of the composition, and the Jujube extract constitutes between about 0.01% to about 1.50% (w/w) of the total weight of the composition.

17. The composition according to claim 16, wherein the Dead Sea extract constitutes about 0.20% (w/w) of the total weight of the composition, the Myrrh tree extract constitutes about 0.50% (w/w) of the total weight of the composition, and the Jujube extract constitutes about 0.50% (w/w) of the total weight of the composition.

18. The composition according to claim 14, wherein said composition is free of *Silybum* extract.

19. The composition according to claim 1, wherein said composition being an anti-glycation composition.

20. The composition according to claim 1, being a topical composition and/or being an anti-aging composition.

21. The composition according to claim 1, being in the form of a serum, a lotion, an ointment, a gel, a moisturizer, a sunscreen, a cream, a stick, a spray, an aerosol, foam, a paste, a mousse, a liquid make-up, a foundation, or a make-up.

22. The composition according to claim 21, formulated as a cosmetic, skin-care, dermatological or a pharmaceutical formulation.

23. The composition according to claim 1, being substantially devoid of Myrrh oil.

24. The composition according to claim 1 for use in one or more of:
- preventing and/or reducing and/or inhibiting the glycation of one or more biomolecules;
- (ii) preventing and/or reducing and/or inhibiting the formation of AGEs (Advanced Glycation End Products);
- (iii) treating and/or preventing at least one disease or disorder of the skin of a subject, wherein said disease or disorder being associate with and/or being induced by glycation of one or more biomolecules and/or formation of AGEs;
- (iv) protecting and/or improving the state of the skin of a subject, wherein said protecting and/or improving the state of the skin of a subject is associated with the compositions capability of preventing and/or reducing and/or inhibiting the glycation of one or more biomolecules, and/or the compositions capability of preventing and/or reducing and/or inhibiting the formation of AGEs;
- (v) preventing and/or treating imperfections of the skin of a subject, wherein said preventing and/or treating imperfections of the skin of a subject is associated with the compositions capability of preventing and/or reducing and/or inhibiting the glycation of one or more biomolecules, and/or the compositions capability of preventing and/or reducing and/or inhibiting the formation of AGEs; and
- (vi) substantially preventing or delaying the onset of, or substantially preventing or retarding the progression of a condition which is associated with the formation of AGEs in a subject in need thereof.

25. A method for preventing and/or reducing and/or inhibiting the glycation of one or more biomolecules and/or for preventing and/or reducing and/or inhibiting the formation of AGEs (Advanced Glycation End Products), the method comprising topical application of a composition according to claim 1 onto at least a region of the skin of a subject.

26. The method according to claim 25, wherein said biomolecule is one or more of at least one protein, at least one lipid or at least one nucleic acid.

27. The method according to claim 26, wherein said at least one protein is a skin protein or an extracellular matrix protein.

28. The method according to claim 25, wherein said AGEs is (i) a protein; and/or (ii) one or more of a carboxymethyl-lysine (CML), a carboxyethyl lysine (CEL), and a fructose-lysine adduct; and/or (iii) pentosidine and/or (iv) at least one extracellular matrix protein.

29. The method according to claim 28, wherein said AGEs is a skin protein; and/or said extracellular matrix protein is one or more of collagen, vimentin and elastin.

30. A method for treating and/or preventing at least one disease or disorder of the skin of a subject, wherein the disease or disorder being associate with and/or being induced by glycation of one or more biomolecules and/or formation of AGEs, the method comprises topical application of the composition according to claim 1 onto the skin of the subject in need thereof.

31. A method for protecting and/or improving the state of the skin of a subject, preventing and/or treating imperfections of the skin of a subject in need thereof, the method comprises topical application of the composition according to claim 1 onto the skin of the subject in need thereof, wherein the protecting and/or improving the state of the skin of a subject, preventing and/or treating imperfections of the skin of a subject in need thereof being associated with the compositions capability of preventing and/or reducing and/or inhibiting the glycation of one or more biomolecules, and/or the compositions capability of preventing and/or reducing and/or inhibiting the formation of AGEs.

32. A method of substantially preventing or delaying the onset of, or substantially preventing or retarding the progression of a condition which is associated with the formation of AGEs in a subject in need thereof, the method comprises administering to the subject a composition according to claim 1.

* * * * *